United States Patent
Nishikawa et al.

(10) Patent No.: US 10,342,987 B2
(45) Date of Patent: Jul. 9, 2019

(54) THERAPEUTIC ELECTROMAGNETIC STIMULATION DEVICE AND METHOD OF GENERATING CUSTOM DATA PAIRS USED IN SAID DEVICE

(75) Inventors: Atsushi Nishikawa, Suita (JP); Youichi Saitoh, Suita (JP); Asao Okada, Suita (JP); Taishi Fukushima, Suita (JP); Taiga Matsuzaki, Chiyoda-ku (JP)

(73) Assignees: OSAKA UNIVERSITY, Suita-shi, Osaka (JP); Teijin Pharma Limited, Chiyoda-ku, Tokyo (JP)

( * ) Notice: Subject to any disclaimer, the term of this patent is extended or adjusted under 35 U.S.C. 154(b) by 283 days.

(21) Appl. No.: 14/114,042

(22) PCT Filed: Apr. 27, 2012

(86) PCT No.: PCT/JP2012/061396
§ 371 (c)(1),
(2), (4) Date: Oct. 25, 2013

(87) PCT Pub. No.: WO2012/147927
PCT Pub. Date: Nov. 1, 2012

(65) Prior Publication Data
US 2014/0046114 A1 Feb. 13, 2014

(30) Foreign Application Priority Data
Apr. 28, 2011 (JP) .................. 2011-102030

(51) Int. Cl.
*A61N 2/02* (2006.01)
*A61B 5/06* (2006.01)
(Continued)

(52) U.S. Cl.
CPC .................. *A61N 2/02* (2013.01); *A61B 5/06* (2013.01); *A61N 2/008* (2013.01); *A61N 2/06* (2013.01)

(58) Field of Classification Search
None
See application file for complete search history.

(56) References Cited

U.S. PATENT DOCUMENTS 7,925,066 B2 * 4/2011 Ruohonen et al. ........... 382/128
2003/0073899 A1 4/2003 Ruohonen et al.
(Continued)

FOREIGN PATENT DOCUMENTS

JP 2003-180649 A 7/2003
JP 2004-636 A 1/2004
(Continued)

OTHER PUBLICATIONS

Extended European Search Report dated Feb. 5, 2015, issued by the European Patent Office in counterpart European application No. 12776684.8.
(Continued)

*Primary Examiner* — Catherine B Kuhlman
(74) *Attorney, Agent, or Firm* — Sughrue Mion, PLLC

(57) ABSTRACT

Provided is a therapeutic electromagnetic stimulation device applying a magnetic field to an object person. The device includes a magnetic field generating means, a magnetic field detecting means, and a data generating means configured to generate custom data pairs for an individual object person. The data generating means is configured to generate the custom data pairs using: a result of detection of intensities in a state in which the magnetic field generating means are disposed respectively at a plurality of sampling spots near a specific site of the object person, and a plurality of parent data pairs each including (a) at least information of a three-dimensional position of the magnetic field generating means pairing with (b) information of the intensities of the corresponding components of the magnetic field at a position having at least the information of the three-dimensional
(Continued)

position, and the information (a) and (b) is previously recorded.

17 Claims, 22 Drawing Sheets

(51) Int. Cl.
*A61N 2/00* (2006.01)
*A61N 2/06* (2006.01)

(56) References Cited

U.S. PATENT DOCUMENTS

| | | |
|---|---|---|
| 2004/0039279 A1 | 2/2004 | Ruohonen |
| 2006/0084860 A1* | 4/2006 | Geiger et al. ............ 600/407 |
| 2008/0161636 A1* | 7/2008 | Hurme et al. ............ 600/13 |
| 2009/0187062 A1 | 7/2009 | Saitoh |
| 2009/0227830 A1* | 9/2009 | Pillutla et al. ............ 600/13 |
| 2010/0185042 A1 | 7/2010 | Schneider et al. |
| 2012/0157752 A1 | 6/2012 | Nishikawa et al. |

FOREIGN PATENT DOCUMENTS

| | | |
|---|---|---|
| JP | 2006-320425 A | 11/2006 |
| WO | 2007/123147 A1 | 11/2007 |
| WO | 2010/147064 A1 | 12/2010 |
| WO | WO 2010147064 A1 * | 12/2010 |

OTHER PUBLICATIONS

International Search Report for PCT/JP2012/061396 dated May 29, 2012.

* cited by examiner

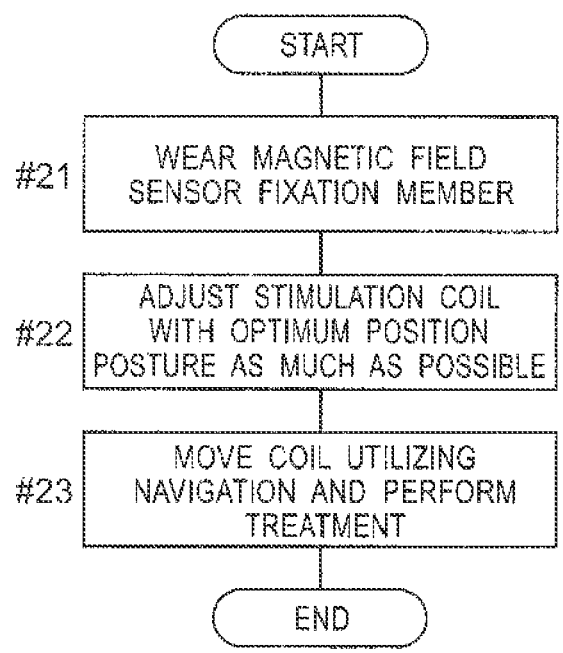
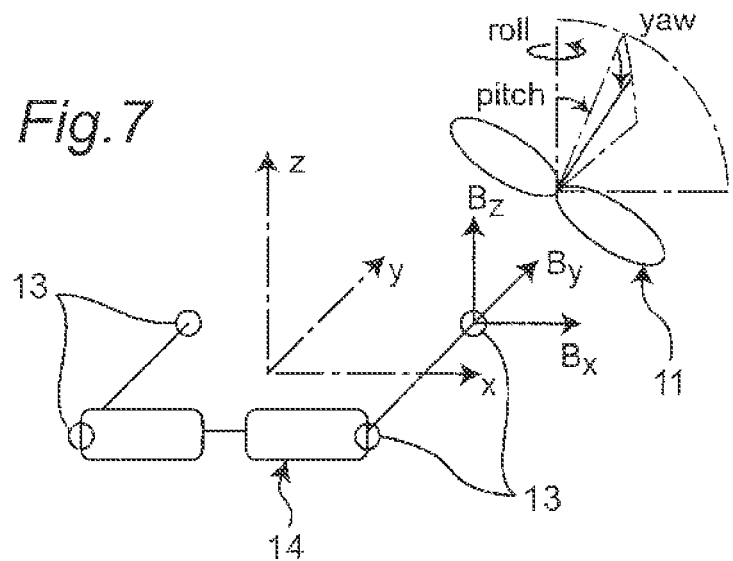

Fig.15
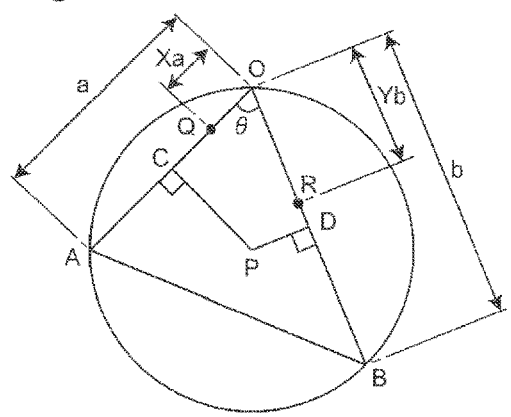
Fig.16
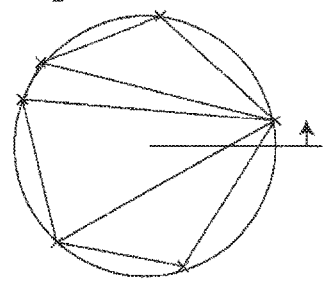
Fig.17
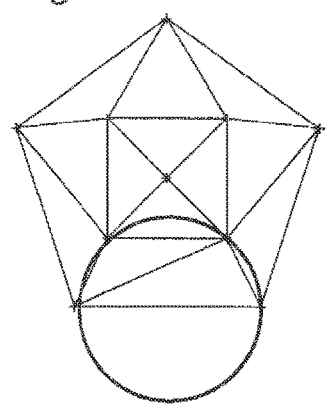
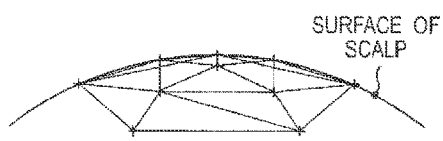
(a) TRIANGULATION RESULT    (b) SURFACE APPROXIMATION RESULT Fig.23
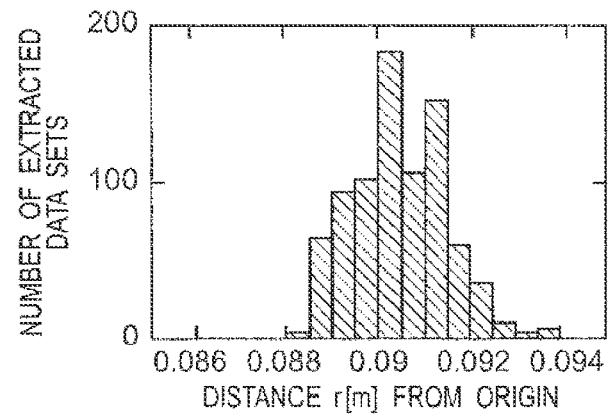
(a) DISTRIBUTION OF DISTANCES
FROM ORIGIN OF GLASS COORDINATE SYSTEM
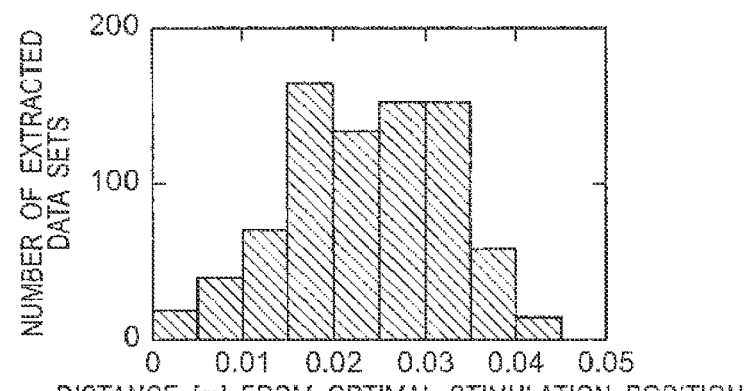
(b) ABSOLUTE DISTRIBUTION OF DISTANCES
FROM OPTIMAL STIMULATION POSITION
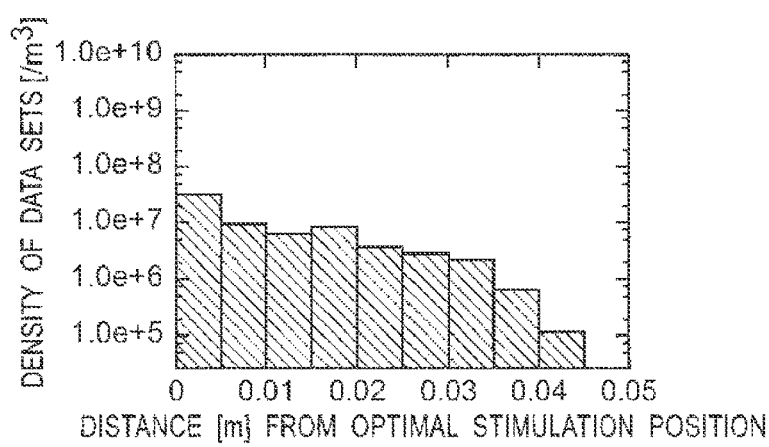
(c) DENSITY DISTRIBUTION OF DISTANCES
FROM OPTIMAL STIMULATION POSITION Fig. 27
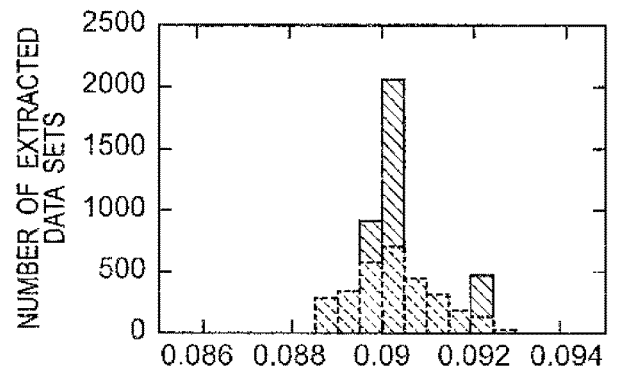
(a) DISTRIBUTION OF DISTANCES FROM ORIGIN OF GLASS COORDINATE SYSTEM
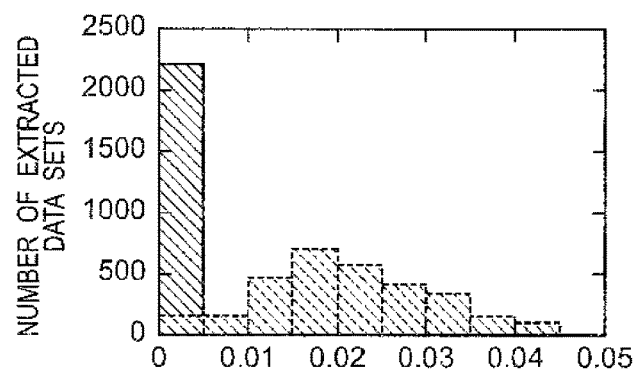
(b) ABSOLUTE DISTRIBUTION OF DISTANCES FROM OPTIMAL STIMULATION POSITION
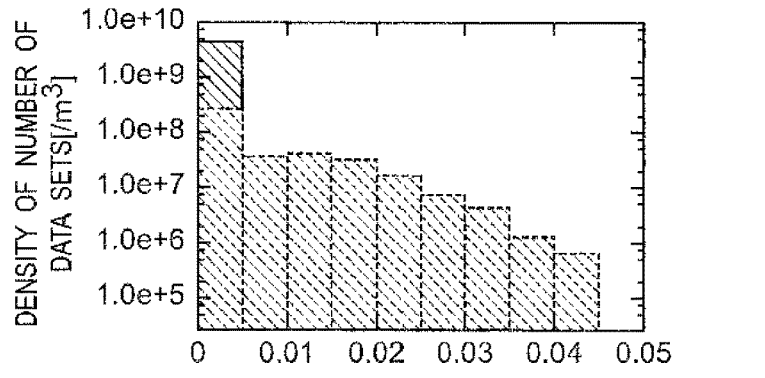
(c) DENSITY DISTRIBUTION OF DISTANCES FROM OPTIMAL STIMULATION POSITION Fig.28
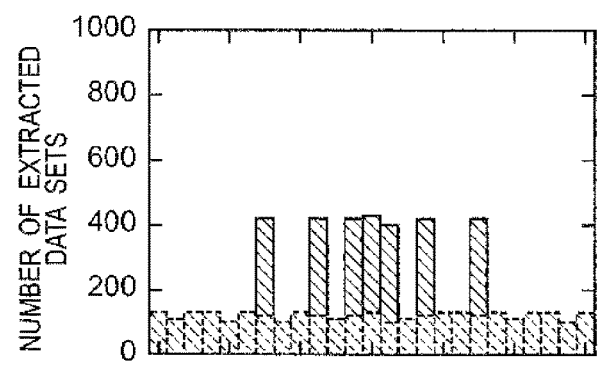
(a) DISTRIBUTION OF roll
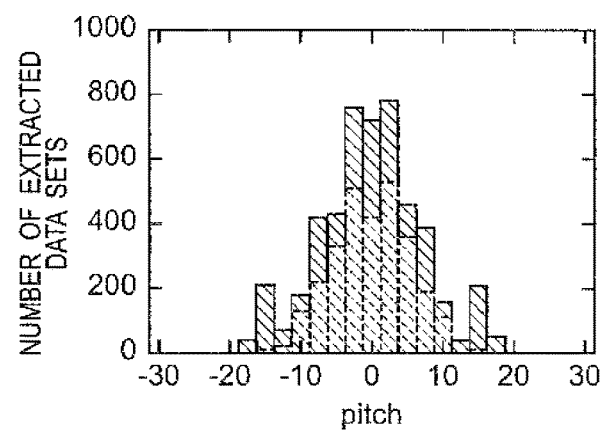
(b) DISTRIBUTION OF pich
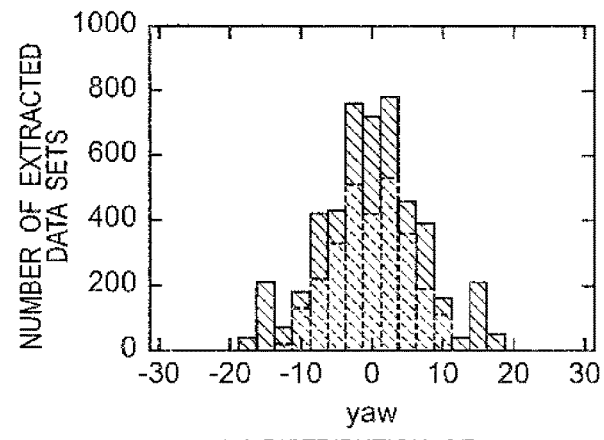
(c) DISTRIBUTION OF yaw Fig.30
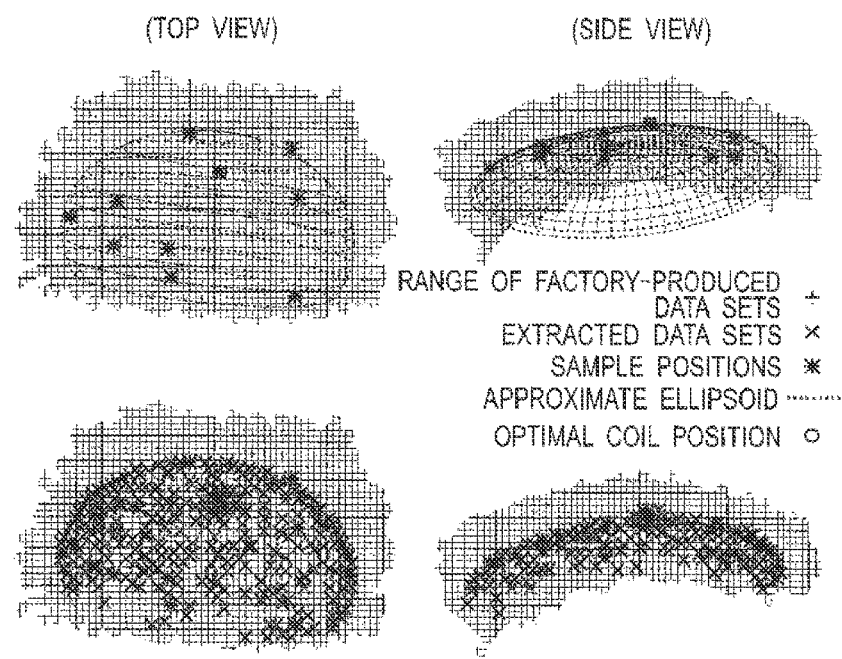
(a) EXTRACTION RESULT USING ELLIPSOIDAL APPROXIMATION
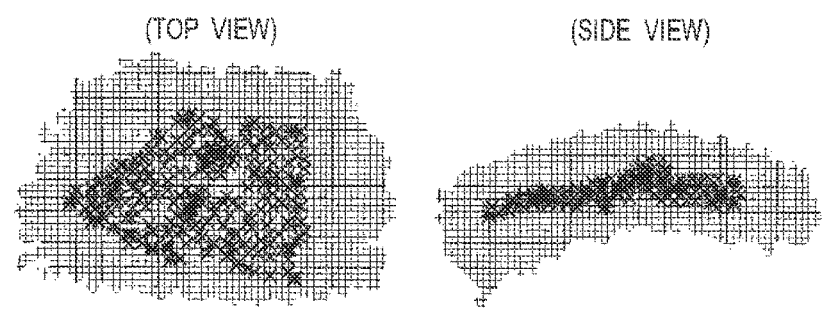
(b) EXTRACTION RESULT USING DELAUNAY TRIANGULATION (a) DELAUNAY TRIANGULATION  (b) ELLIPSOIDAL APPROXIMATION Fig.32
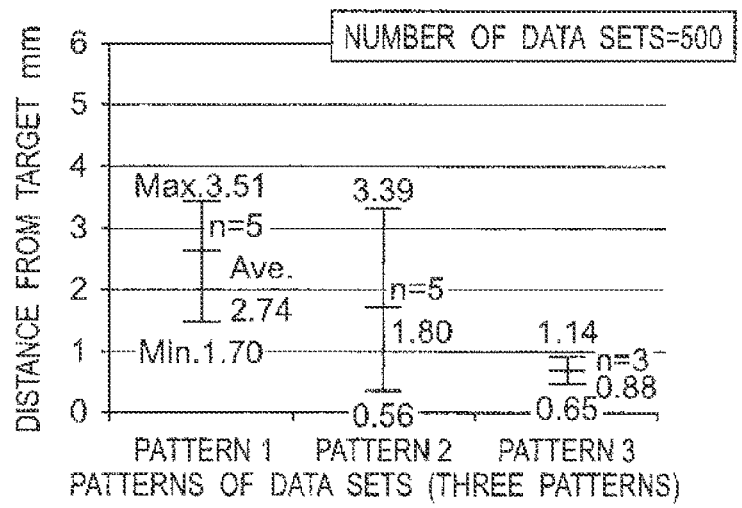
(a) DEVIATION BETWEEN ACTUAL MEASUREMENT
VALUES AND ESTIMATION VALUES
(MEASUREMENT ACCURACY ON COMPLETION OF NAVIGATION)
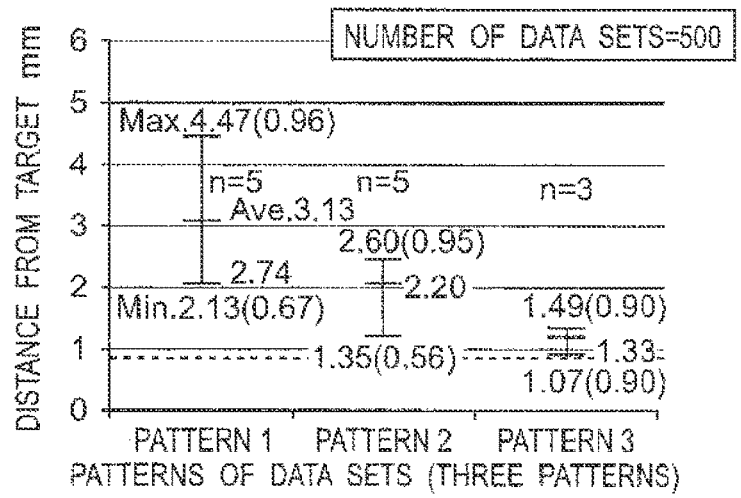
(b) DEVIATION BETWEEN ACTUAL MEASUREMENT
VALUES AND TARGET
(NAVIGATION ACCURACY OF SYSTEM)

THERAPEUTIC ELECTROMAGNETIC STIMULATION DEVICE AND METHOD OF GENERATING CUSTOM DATA PAIRS USED IN SAID DEVICE

CROSS REFERENCE TO RELATED APPLICATIONS

This application is a National Stage of International Application No. PCT/JP2012/061396 filed Apr. 27, 2012, claiming priority based on Japanese Patent Application No. 2011-102030 filed Apr. 28, 2011, the contents of all of which are incorporated herein by reference in their entirety.

TECHNICAL FIELD

The present invention relates to a therapeutic electromagnetic stimulation device for providing magnetic stimulation by applying a magnetic field to a specific site on an object person (e.g., a subject such as a patient or a person receiving checkups), and a method of generating custom data pairs used in this device for each object person.

BACKGROUND ART

In recent years, a transcranial magnetic stimulation treatment is increasingly receiving attentions as a treatment method to patients of various neural diseases for which medication is not always effective. The transcranial magnetic stimulation treatment is a relatively new treatment method capable of applying magnetic stimulation to a particular region of the brain (brain nerve, for example) by a magnetic field generating source provided on the surface of a patient's scalp, thereby providing a treatment and/or relieving symptoms. Unlike the conventional electric stimulation requiring a craniotomy procedure and using an implanted electrode that makes a patient highly uncomfortable, the transcranial magnetic stimulation treatment is expected to be broadly used as a treatment method that is non-invasive and less stressful for patients.

As a specific method of such a transcranial magnetic stimulation treatment, there is known a method of applying electrical current to a coil provided on the surface of a patient's scalp, regionally generating a small pulsed magnetic field, generating eddy current within a cranium based on a principle of electromagnetic induction, and applying stimulation to the brain nerve immediately under the coil (see Patent Literature 1, for example).

According to Patent Literature 1, it is confirmed that the transcranial magnetic stimulation treatment provided according to the above method effectively relieves intractable neuropathic pains, and in addition, provides a higher effect for pain relief by applying focal stimulation more accurately. However, it is also disclosed that optimum stimulating regions of individual patients are slightly different.

Therefore, in order to achieve a higher effect with the transcranial magnetic stimulation treatment, it is important how an optimum stimulating region on a patient's head is determined for each patient, or more specifically, how three-dimensional positioning of a magnetic coil to the patient's head is performed accurately. It should be noted that it is also known that even if the position of the magnetic coil is the same, an achieved effect varies depending on an orientation (posture) of the coil.

Known configurations of the positioning of such a magnetic coil include positioning of a magnetic coil on the patient's head utilizing an optical tracking system using infrared rays (see Patent Literatures 2 and 3, for example), and some are commercially available and applied in clinical settings. In addition, Patent Literature 4 discloses a device capable of positioning a magnetic coil on the patient's head using an articulated robot.

Further, Patent Literature 1 also discloses that a pain relief effect by performing the transcranial magnetic stimulation treatment described above lasts for on the order of several hours, but not for days or longer. Therefore, in terms of the pain relief, it is considered to be desirable to perform the treatment continuously, without taking a long interval, preferably every day. In order to allow such a continuous treatment to be performed without imposing too much burden on a patient such as physically and in terms of time, it is ideal that a treatment at home or at a personal doctor's office in the neighborhood be made possible.

However, all of the conventional transcranial magnetic stimulators including devices and systems for coil positioning as described above are intended to be used in a relatively large-scale hospital or a research institute for an examination or a research by skillful specialized physicians. Accordingly, such devices are complicated in handling and operation, require a lot of skill to use, and are quite large-scaled and expensive. For this reason, it is generally difficult for a patient, a family member of the patient, or the patient's personal doctor in the neighborhood who is not necessarily an expert at the magnetic stimulation to perform a treatment by operating the stimulator. In addition, in order to install the stimulator at the patient's own house, a relatively small-scale doctor's office, a clinic, or such, the cost is too much and it is also generally difficult to secure an installation space.

Therefore, patients taking the transcranial magnetic stimulation treatment have no choice but to visit a large hospital having a large-scale magnetic stimulator installed and skillful specialized physicians every time taking the treatment, or to stay in the hospital, and are forced to bear a large burden in various aspects in order to take the treatment continuously and repeatedly.

Thus, the inventors of this application have proposed, in Patent Literature 5, a smaller and less expensive magnetic stimulator that can be easily handled and operated and allows a patient to perform a transcranial magnetic stimulation treatment continuously and repeatedly on a daily basis at home, a personal doctor's office in the neighborhood, or such. Further, as a method of guiding the magnetic coil to the three-dimensional position and posture corresponding to the optimum position and posture at which the magnetic stimulation is to be applied using such an electromagnetic stimulation device, the inventors have proposed a method of guiding the magnetic coil to the three-dimensional position and posture corresponding to the optimum position and posture, for example, by additionally providing a magnetic field generating means such as a permanent magnet for a coil holder of the magnetic coil, and by utilizing a set of pieces of data combining as a pair the data of at least the position (preferably, the position and posture) of the magnetic field generating means, and the data relating to the intensity and direction of the magnetic field generated at this position and detected by the magnetic field detecting means such as a magnetic sensor. As used herein, the set of pieces of data is referred to as a "data pair" or a "data set" as appropriate.

The method of guiding the magnetic coil utilizing the data set involves a problem that it is necessary to collect a large number of data sets (at least on the order of 500 sets) for each patient previously in the hospital, and the collection of the data sets results in a significant burden for the doctor.

In this regard, Patent Literature 5 has proposed that a collecting operation of data sets is divided into a part that may be carried out only by the doctor and a part that can be carried out by a person other than the doctor, and that the collecting operation of the data sets other than the determination of the optimum stimulation position and posture is performed, for example, as a part of a pre-shipment examination by a manufacturer (maker) of the electromagnetic stimulation device separately from the determination of the optimum stimulation position and posture by the doctor in the hospital.

PATENT LITERATURES

Patent Literature 1: WO 2007/123147 A
Patent Literature 2: JP 2003-180649 A
Patent Literature 3: JP 2004-000636 A
Patent Literature 4: JP 2006-320425 A
Patent Literature 5: WO 2010-147064 A

SUMMARY OF THE INVENTION

Problems to be Solved by the Invention

By performing the collecting operation of a large number of data sets other than the collection of a relatively smaller number of data sets (hereinafter referred to as sample data sets as appropriate) required for the determination of the optimal stimulation position and posture separately from the collection of the data sets by the doctor in the hospital, it is possible to significantly reduce the burden for the doctor involved in the collection of data sets. However, there is a problem that it takes an extended period of time for guiding the magnetic coil if a simple comparison with all of the large number of data sets is made by comparing sample data sets collected by the doctor with a large number of data sets previously collected by, for example, the manufacturer, and obtaining the three-dimensional position and posture of the magnetic coil corresponding to the optimal stimulation position and posture, and it is not practical.

Therefore, it is conceivable to reduce time required for guiding the magnetic coil by extracting data sets within an appropriate range required for guiding the magnetic coil to the three-dimensional position and posture corresponding to the optimal stimulation position and posture from a large number of data sets previously collected by, for example, the manufacturer, and to comparing the extracted data sets within this range with the sample data sets collected by the doctor. In this case, how to extract the data sets within the appropriate range from the large number of previously collected data sets is an important issue.

The present invention is made in view of the above problems, and an object of the present invention is fundamentally to allow extraction, from a large number of previously collected data sets, of data sets within an appropriate range required for obtaining three-dimensional position and posture of a magnetic coil corresponding to optimal stimulation position and posture depending on a shape of a surface of a scalp of the patient, when guiding a magnetic coil to three-dimensional position and posture corresponding to optimal stimulation position and posture utilizing the data sets.

Means for Solving the Problems

A therapeutic electromagnetic stimulation device according to the present invention is for providing magnetic stimulation by applying a magnetic field to a specific site of an object person, the device including: a magnetic field generating means configured to generate one of a therapeutic magnetic field and a detection magnetic field for detection of information at least including positional information; magnetic field detecting means respectively disposed so as to take specific relative position with respect to the object person in order to detect intensities of components in a plurality of directions of one of the therapeutic magnetic field and the detection magnetic field at least at two detection positions; and a data generating means configured to generate custom data pairs for an individual object person, the custom data pairs being for deriving at least information of positions of the magnetic field generating means from the intensities of the corresponding components, the data generating means generating the custom data pairs using: (1) a sampling detection result of the detection of the intensities of the corresponding components in a state in which the magnetic field generating means are disposed respectively at a plurality of sampling spots near the specific site of the object person; and (2) a plurality of parent data pairs each including (a) at least information of a three-dimensional position of the magnetic field generating means pairing with (b) information of the intensities of the corresponding components of the magnetic field at a position having at least the information of the three-dimensional position, the information (a) and (b) being previously recorded.

In this case, the therapeutic electromagnetic stimulation device may further include an information generating means configured to generate, using the generated custom data pairs and the result of the detection of the intensities of the corresponding components of the magnetic field performed when performing a treatment, one of (A) information instructing an operation for moving the magnetic field generating means in order to apply magnetic stimulation to the specific site if the magnetic field generating means are configured movably according to an operation, and (B) information for controlling a movement if a moving means configured to move the magnetic field generating means to a position for an application of magnetic stimulation to the specific site is provided.

In the above-described cases, the specific site may be a specific stimulation position within a head of the object person, and the data generating means may refer to the parent data pairs based on the sampling detection result, approximate a shape of a surface of a scalp of the object person, and extract a plurality of data pairs close to the approximated shape of the scalp as the custom data pairs from the parent data pairs.

In this case, the approximation of the shape of the surface of the scalp of the object person may be performed based on Delaunay triangulation. Alternatively, the approximation of the shape of the surface of the scalp of the object person may be performed based on ellipsoidal approximation.

Moreover, in the above-described case, the detection magnetic field may be for detection of positional information and angle information, the magnetic field detecting means may be disposed to take specific relative positions and specific relative angles with respect to the object person, the parent data pairs each include (a') information of a three-dimensional position and an inclination angle of the magnetic field generating means pairing with (b') information of the intensities of the corresponding components of the magnetic field at the position and the inclination angle, and the data generating means may generate the custom data pairs for an individual object person, the custom data pairs being for deriving the information of the position and the inclination angle of the magnetic field generating means.

Alternatively, the detection magnetic field may be for detection of positional information, the magnetic field detecting means may be disposed to take specific relative positions and specific relative angles with respect to the object person, the parent data pairs each include (a') information of a three-dimensional position and an inclination angle of the magnetic field generating means pairing with (b') information of the intensities of the corresponding components of the magnetic field at the position and the inclination angle, the data generating means generates the custom data pairs for an individual object person, the custom data pairs being for deriving the information of the position and the inclination angle of the magnetic field generating means, and the detection of the inclination angle of the magnetic field generating means may be performed by a measuring means configured to measure the inclination angle of the magnetic field generating means separately from the generation and the detection of the detection magnetic field.

Furthermore, the method of generating custom data pairs according to the present invention is to be used for a therapeutic electromagnetic stimulation device for providing magnetic stimulation by applying a magnetic field to a specific site of an object person, the device being provided with: a magnetic field generating means configured to generate one of a therapeutic magnetic field and a detection magnetic field for detection of information at least including positional information; and magnetic field detecting means respectively disposed so as to take specific relative position with respect to the object person in order to detect intensities of components in a plurality of directions of one of the therapeutic magnetic field and the detection magnetic field at least at two detection positions, the method including: a sampling detection step of detecting the intensities of the corresponding components in a state in which the magnetic field generating means are disposed respectively at a plurality of sampling spots near the specific site of the object person; a step of referring to a plurality of previously recorded parent data pairs based on the sampling detection result, the plurality of parent data pairs each including (a) at least information of a three-dimensional position of the magnetic field generating means pairing with (b) information of the intensities of the corresponding components of the magnetic field at a position having at least the information of the three-dimensional position; and a step of generating custom data pairs for an individual object person, the custom data pairs being for deriving at least information of positions of the magnetic field generating means from the intensities of the corresponding components.

In this method, the specific site may be a specific stimulation position within a head of the object person, and a data generating means may refer to the parent data pairs based on the sampling detection result, approximate a shape of a surface of a scalp of the object person, and extract a plurality of data pairs close to the approximated shape of the scalp as the custom data pairs from the parent data pairs.

In this case, the approximation of the shape of the surface of the scalp of the object person may be performed based on Delaunay triangulation. Alternatively, the approximation of the shape of the surface of the scalp of the object person may be performed based on ellipsoidal approximation.

Moreover, in the above-described methods, the detection magnetic field may be for detection of positional information and angle information, the magnetic field detecting means may be disposed to take specific relative positions and specific relative angles with respect to the object person, the parent data pairs each include (a') information of a three-dimensional position and an inclination angle of the magnetic field generating means pairing with (b') information of the intensities of the corresponding components of the magnetic field at the position and the inclination angle, and in the step of generating the custom data pairs, the custom data pairs for deriving the information of the position and the inclination angle of the magnetic field generating means may be generated for an individual object person.

Alternatively, the detection magnetic field may be for detection of positional information, the magnetic field detecting means may be disposed to take specific relative positions and specific relative angles with respect to the object person, the parent data pairs each include (a') information of a three-dimensional position and an inclination angle of the magnetic field generating means pairing with (b') information of the intensities of the corresponding components of the magnetic field at the position and the inclination angle, in the step of generating the custom data pairs, the custom data pairs for deriving the information of the position and the inclination angle of the magnetic field generating means are generated for an individual object person, and the detection of the inclination angle of the magnetic field generating means may be performed by a measuring means configured to measure the inclination angle of the magnetic field generating means separately from the generation and the detection of the detection magnetic field.

Effects of the Invention

According to the present invention, when providing magnetic stimulation by applying a magnetic field to a specific site of an object person, by referring to a plurality of previously recorded parent data pairs each including (a) at least information of a three-dimensional position of the magnetic field generating means pairing with (b) information of the intensities of the corresponding components of the magnetic field at a position having at least the information of the three-dimensional position based on the sampling detection result of detection of the intensities of the corresponding components in a state in which the magnetic field generating means are disposed respectively at a plurality of sampling spots near the specific site of the object person, and by generating custom data pairs for an individual object person, the custom data pairs being for deriving at least information of positions of the magnetic field generating means from the intensities of the corresponding components, it is possible to, according to the object person, extract data pairs within an appropriate range for obtaining at least the three-dimensional position of the magnetic field generating means corresponding to at least the optimal stimulation position. Then, prior to the magnetic stimulation or during the magnetic stimulation, by comparing the information of the intensities and the directions of the magnetic field detected by each magnetic field detecting means with the custom data pairs, it is possible to guide the magnetic field generating means to the three-dimensional position corresponding to at least the optimal stimulation position without requiring an extended period of time as conventionally required.

BRIEF DESCRIPTION OF THE DRAWINGS

FIG. 6 is a flowchart explaining the operation method of the transcranial magnetic stimulator in a home treatment.

FIG. 7 is an explanatory diagram illustrating a glass coordinate system according to the embodiment.

FIG. 15 is an explanatory diagram illustrating a position of a circumcenter of a triangle related to Delaunay triangulation.

FIG. 16 is an explanatory diagram illustrating Delaunay triangulation when there are four or more samples concyclically along the same circle.

FIG. 17 is an explanatory diagram illustrating a result of Delaunay triangulation to 10 samples.

FIG. 23 shows explanatory charts illustrating distribution of data sets when the data set extraction near the approximate surface of the scalp is performed.

FIG. 27 shows a part of explanatory charts illustrating distribution of data sets in the data set extraction when the density adjustment is performed.

FIG. 28 shows a part of explanatory charts illustrating distribution of data sets in the data set extraction when the density adjustment is performed.

FIG. 30 shows explanatory diagrams illustrating data set extraction results using 10 samples, in which (a) shows an extraction result using the ellipsoidal approximation, and (b) shows an extraction result using Delaunay triangulation.

FIG. 32 shows explanatory charts illustrating experimentation results of a navigation experiment, in which (a) is a chart showing deviation between actual measurement values and estimation values, and (b) is a chart showing deviation between actual measurement values and targets.

EMBODIMENTS OF THE INVENTION

One embodiment of the present invention is now described with reference to the drawings.

Figure 1:
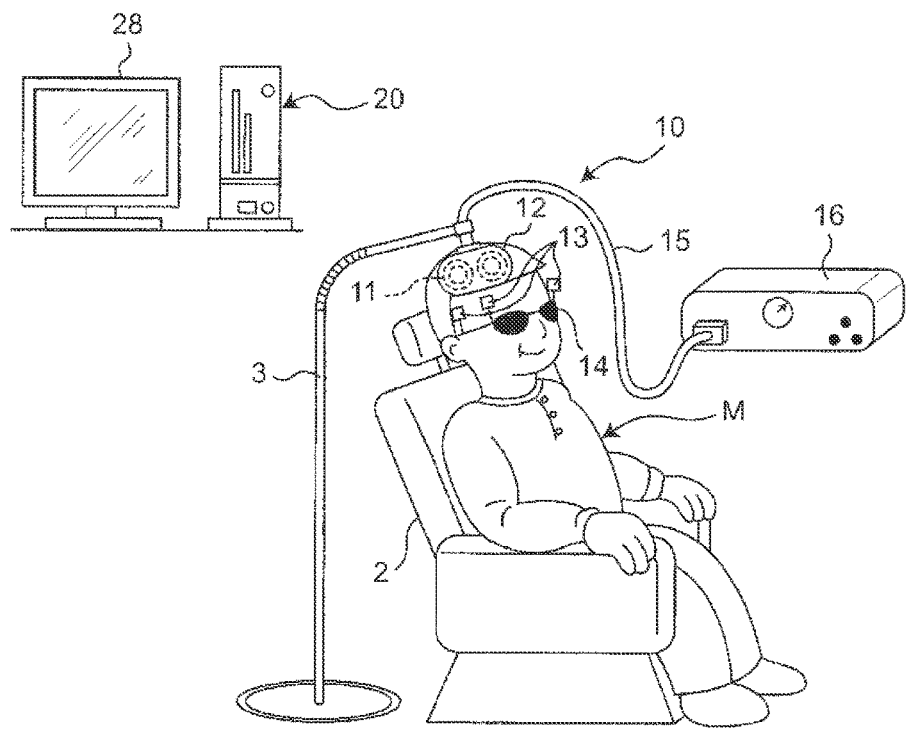
FIG. 1 is an explanatory view schematically illustrating an overall configuration of a transcranial magnetic stimulator according to one embodiment of the present invention.

FIG. 1 is an explanatory view schematically illustrating an overall configuration of a transcranial magnetic stimulator according to this embodiment. In the drawing, a transcranial magnetic stimulation apparatus (hereinafter referred to as an "electromagnetic stimulation device" or simply to "device", accordingly) as a whole represented by a reference numeral 10 is intended to perform a treatment and/or to relieve symptoms by applying magnetic stimulation to brain nerve using a magnetic coil 11 placed on the surface of a scalp of a patient M (subject) statically seated in a therapeutic chair 2. It should be noted that the magnetic coil corresponds to a "magnetic field generating means" defined in the appended claims.

The magnetic coil 11 is configured to generate a dynamic magnetic field for applying a magnetic stimulation to a particular region of the brain of the patient M, and attached to a coil holder 12 that can be manipulated displaceably with respect to a surface of the head of the patient M.

It should be noted that FIG. 1 shows a state in which the coil holder 12 is fixed preferably to a holder fixation member 3 so that the coil 11 does not move unintentionally after the coil 11 has been positioned by displacing the magnetic coil 11 along the patient's scalp while holding the coil holder 12.

Figure 2:
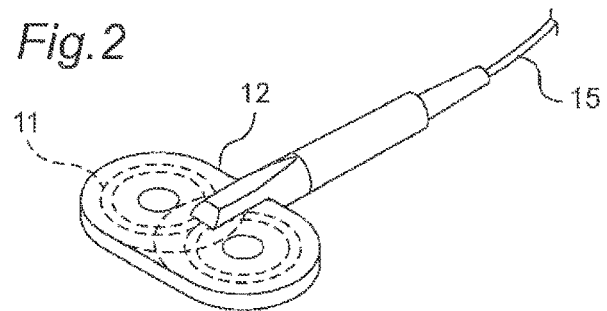
FIG. 2 is a perspective view illustrating one example of a magnetic coil and a coil holder used in the embodiment.

Examples of the magnetic coil 11 to be used include various types of known magnetic coils. FIG. 2 is a perspective view illustrating one example of the magnetic coil capable of being used as a dynamic magnetic field generating means for a transcranial magnetic stimulation treatment and the coil holder according to this embodiment. The magnetic coil 11 shown in FIG. 2 is a so-called figure-eight spiral coil configured by two spiral coils arranged in the figure of eight in the same plane, and its induction current density is maximum immediately under a portion corresponding to an intersection of the figure of eight. The magnetic coil 11 of this type is somewhat difficult to be fixed including determination of its posture, but suitable for applying localized stimulation. The magnetic coil 11 is preferably resin-molded monolithically with the coil holder 12 when molding the coil holder 12 made of synthetic resin. Further, eccentric coils may be used for both of the two spiral coils such that winding becomes dense in a direction corresponding to an intersection in the figure of eight. In this case, it is possible to produce an induction current more effectively immediately under a point corresponding to the intersection in the figure of eight.

The magnetic coil 11 is electrically connected to a magnetic stimulation control device 16 via a cable 15. The magnetic stimulation control device 16 is configured to control supply of a current pulse to the magnetic coil 11, and various types of conventionally known devices can be used. ON/OFF manipulation of the magnetic stimulation control device 16 is performed by an operator. Further, setting of intensity and a pulse waveform of the current pulse for determining intensity and a cycle of magnetic stimulation can also be performed by the operator.

In this embodiment, as a magnetic field detecting means for detecting a magnetic field generated by the magnetic coil 11, a pair of front and rear magnetic field sensors 13, for example, so-called triaxial sensors are provided for either side of a frame on left and right of a pair of eyeglasses 14 (total four) that the patient M is wearing. With this, the magnetic field may be detected (an intensity of the magnetic field and a direction of the magnetic field may be detected) at four points at front, rear, left, and right surrounding the head of the patient M.

Examples of the magnetic field sensors 13 to be used include various types of known magnetic field sensors (magnetic sensors) such as an inductive sensor such as a so-called search coil, a Hall sensor utilizing a Hall effect, an MR sensor utilizing a magnetoresistance effect, an MI sensor utilizing a magneto-impedance, and a fluxgate sensor, for example. Many of mass-produced sensors of a few millimeters (mm) square and a few grams (g) can be purchased for about a few hundred yen per piece. It is possible to obtain sensors that are sufficiently downsized, lightweight, and low-cost as those used in the transcranial magnetic stimulation treatment.

The pair of eyeglasses 14 serves as a fixing means (that is, a magnetic field sensor fixation member) configured to fix positions of the plurality of magnetic field sensors 13 (four, for example, in this embodiment) with respect to the patient's head. The positions at which the magnetic field sensors 13 are to be fixed on the head of the patient M are required to be reproducible, and it is necessary to fix the magnetic field sensors 13 always at the same positions on the patient M. It is desirable to use a familiar appliance (body fitment) that can be frequently worn on a daily basis as a means for fixing the magnetic field sensors 13 on the patient's head in a relatively natural manner without giving an uncomfortable or unpleasant feeling to the patient M while ensuring repeatability and reproducibility of the positions to be fixed. In this point, the pair of eyeglasses 14 is suitable. It should be noted that while a position of a pair of eyeglasses used commonly can be often slightly displaced upward or downward, a so-called pair of protective (safety) glasses and goggles for sporting are designed so as not to easily displaced, and are particularly suitable as an attachment appliance for the magnetic field sensors 13. Further, body accessories such as a pair of earpieces, a pair of headphones, or a headband may be suitably used.

In this embodiment, the four magnetic field sensors 13 are attached to the pair of eyeglasses 14 as the magnetic field sensor fixation member. However, the number of the magnetic field sensors 13 is not limited to four. As is well known, the larger the number of the sensors, the more preferable in order to improve measurement accuracy in general. However, this also increases complexity of the system as well as the costs. Accordingly, it is desired to reduce the number of the sensors as much as possible. Even in this case, in order to ensure measurement accuracy above a certain level, it is preferable to use at least two sensors, and more preferably, these sensors are arranged isotropically with respect to the patient's head.

In this embodiment, when guiding the magnetic coil to the three-dimensional position and posture corresponding to the optimal stimulation position and posture utilizing the data sets, as will be described later in detail, the burden for the doctor involved in conventional collection of data sets is significantly reduced by performing a collecting operation of a large number of data sets separately from the collection of magnetic field data by the doctor in the hospital other than collection of a relatively smaller number of magnetic field data required for determination of the optimal stimulation position and posture. The collection of the large number of data sets performed separately from the collection of the magnetic field data by the doctor in the hospital is performed, for example, as a part of a pre-shipment examination by a manufacturer (maker) of the electromagnetic stimulation device. As used herein, the large number of data sets thus collected by the manufacturer are referred to as "factory-produced data sets". The factory-produced data sets correspond to "parent data pairs" defined in the appended claims.

It should be noted that the collection of the large number of data sets performed separately from the collection of the magnetic field data by the doctor in the hospital is not limited to a case of being performed by the manufacturer itself, and may be performed, for example, by a subcontractor and the like outsourced by the manufacturer or the hospital.

Here, taking a case of an application to a treatment of neuropathic pain, for example, "the optimal stimulation position and posture" are the optimum position (so-called sweet spot) and posture of the coil at which the neuropathic pain of the patient M can be most effectively relieved when applying the magnetic stimulation to the specific site of the brain of the patient M using the magnetic coil 11, and can be determined when performing a treatment in the hospital such as in an initial treatment.

In the hospital, by comparing the magnetic field data (data relating to an intensity and a direction of the magnetic field) obtained by detecting a magnetic field of the magnetic coil 11 by the magnetic field sensors 13 with the factory-produced data sets, it is possible to learn the position and the posture of the magnetic coil 11 with respect to the produced magnetic field, and to record the magnetic field data of the magnetic coil 11. Specifically, the magnetic field data is collected and recorded for the optimal stimulation position and posture determined by the doctor according to the conventional method and a plurality of (relatively small, for example, on the order of 10) positions and postures around the optimal position and posture. As used herein, the magnetic field data thus collected by the doctor in the hospital is referred to as "sample magnetic field data" as appropriate.

If the factory-produced data sets in a sufficiently high density are prepared by the manufacturer, only by the doctor in the hospital determining the optimal stimulation position and posture using the magnetic coil 11 and the magnetic field sensors 13, the three-dimensional position and posture corresponding to the magnetic field at this time (values called from the factory-produced data sets) referring to the factory-produced data sets prepared by the manufacturer may be taken as the optimal stimulation position and posture as they are without going through a coordinate conversion process or the like. In this case, this means that the coordinate conversion process between coordinate systems on the side of the manufacturer and the side of hospital is performed utilizing the data sets.

It should be noted that instead of detecting a dynamic magnetic field produced by the magnetic coil 11 as described above, it is possible to provide the coil holder 12 holding the magnetic coil 11 with a permanent magnet and to detect a static magnetic field produced by the permanent magnet by the magnetic field sensors 13 to obtain the magnetic field data.

The transcranial magnetic stimulation apparatus 10 according to this embodiment is provided with a data set analyzing unit in order to guide the magnetic coil to the three-dimensional position and posture corresponding to the optimal stimulation position and posture by utilizing the data sets.

Figure 3:
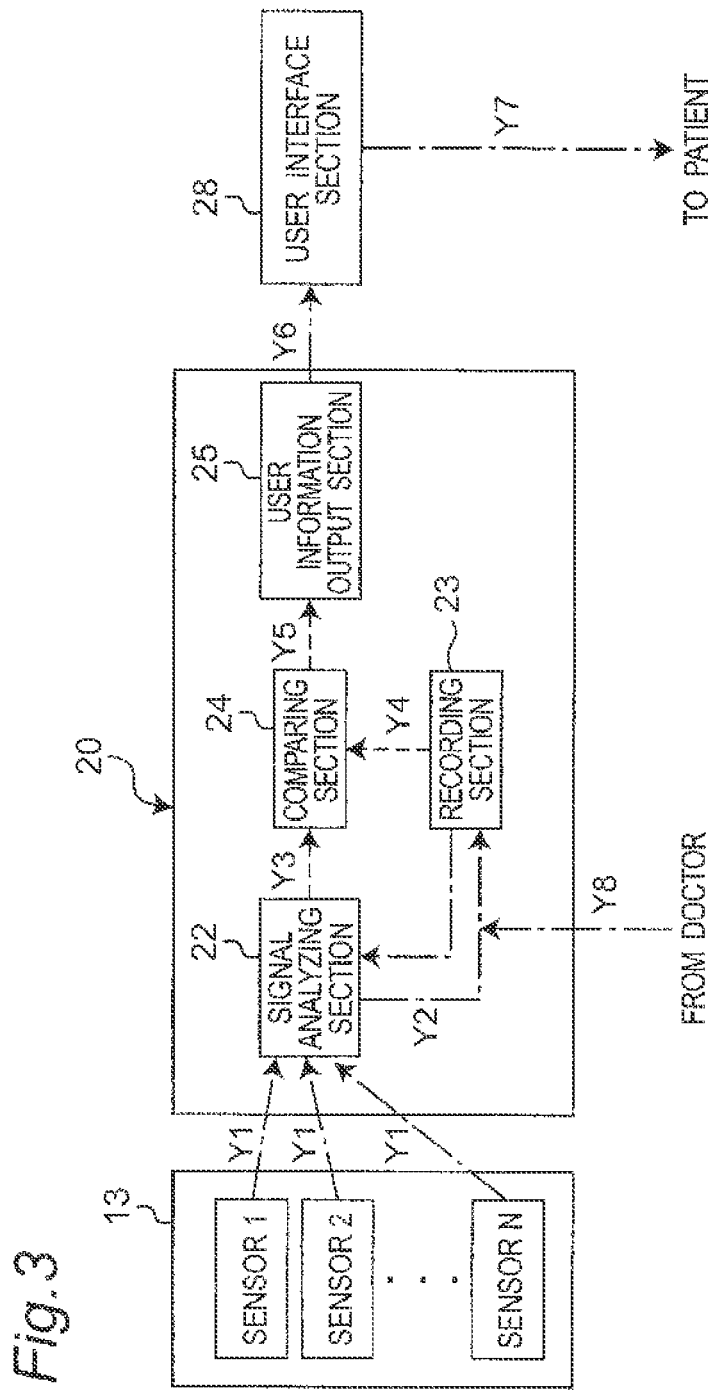
FIG. 3 is a block diagram schematically illustrating a configuration of a data set analyzing unit used in the embodiment.

FIG. 3 is a block configurational diagram schematically illustrating a configuration of a data set analyzing unit 20 used in embodiment. The data set analyzing unit 20 is configured by a so-called personal computer having a CPU (Central Processing Unit) as a main section, for example, and as shown in the block diagram of FIG. 3, is provided with a signal analyzing section 22, a recording section 23, a comparing section 24, and a user information output section 25.

Further, the data set analyzing unit 20 is provided with a display device 28 having a display panel of a liquid crystal type, for example. The display device 28 serves as an interface for, after obtaining current position and posture of the magnetic coil 11 utilizing the data sets, providing the user with the current position and posture of the coil 11, and guiding the magnetic coil 11 to an optimum position (that is, a position corresponding to an optimum stimulating region) and posture. It should be noted that the "user" in this case refers to the patient, a family member of the patient, a doctor or medical staff at a personal doctor's office, or others, for example.

The signal analyzing section 22 is configured to, based on detection signals inputted from the plurality of magnetic field sensors 13 (sensor 1, sensor 2, . . . , and sensor N) that are inputted preferably as wireless signals (see an arrow Y1 in FIG. 3), obtain the magnetic field data of the magnetic field produced by the magnetic coil 11 (the data relating to the intensity and the direction of the magnetic field), and input the magnetic field data to the recording section 23 (see an arrow Y2 in FIG. 3).

The recording section 23 is configured as a readable memory device, and having a large number of factory-produced data sets previously collected by the manufacturer recorded in advance before shipment from the manufacturer. The recording section 23 also records the magnetic field data collected (sample magnetic field data), when performing a treatment in the hospital such as in an initial treatment, for the optimal stimulation position and posture determined by the doctor according to the conventional method and the plurality of (for example, on the order of 10) positions and postures around thereof (see an arrow Y8 in FIG. 3).

It should be noted that it is preferable to collect an extremely large number of data sets as the factory-produced data sets, in order to treat every patient.

The comparing section 24 extracts, from the factory-produced data sets, data sets smaller than the factory-produced data sets and including a data set group corresponding to the sample magnetic field data (hereinafter referred to as "extracted data set") using the sample magnetic field data and the factory-produced data sets that are both recorded in the recording section 23.

The extracted data sets are extracted as a data set group by approximating the surface of the scalp of the examinee based on the three-dimensional position of each data set in the data set group corresponding to the sample magnetic field data to the shape of the surface of the scalp. The extracted data set is also recorded in the recording section 23.

Then, the comparing section 24 compares, prior to the magnetic stimulation or during the magnetic stimulation, the magnetic field data (each information relating to the intensity and the direction of the magnetic field) detected by each of the magnetic field sensors 13 and inputted to the signal analyzing section 22 with the extracted data set recorded in the recording section 23 (see arrows Y3 and Y4 in FIG. 3). With this, it is possible to detect the deviation (misalignment) of the data set corresponding to the magnetic field data obtained by the signal analyzing section 22 from the data set of the optimal stimulation position and posture.

Then, a signal of the deviation data sensed based on a result of the comparison by the comparing section 24 is outputted to a user interface unit 28 (the display device in this embodiment) via the user information output section 25 (see arrows Y5 and Y6 in FIG. 3). The user interface unit 28 is configured to generate, based on the outputted signal from the user information output section 25, instruction information indicating an operation of displacement to be performed using an operating means (the coil holder 12) (in the case of the display device, a signal for displaying such as a video signal), and provides the user with the generated information.

The operator (user) of the device 10 manipulates the coil holder 12 to displace along the scalp of the patient M while watching the display device 28 (see an arrow Y7 in FIG. 3) such that the deviation shown in a screen of the display device 28 is close to zero as much as possible. Then, the manipulation of the magnetic coil 11 to displace is stopped at the position and posture of the magnetic coil 11 at which the deviation shown in the screen of the display device 28 is zero or close to zero as much as possible, and this state is maintained. It should be noted that at this time, as shown in FIG. 1, it is convenient to fix the coil holder 12 using the holder fixation member 3.

Figure 4:
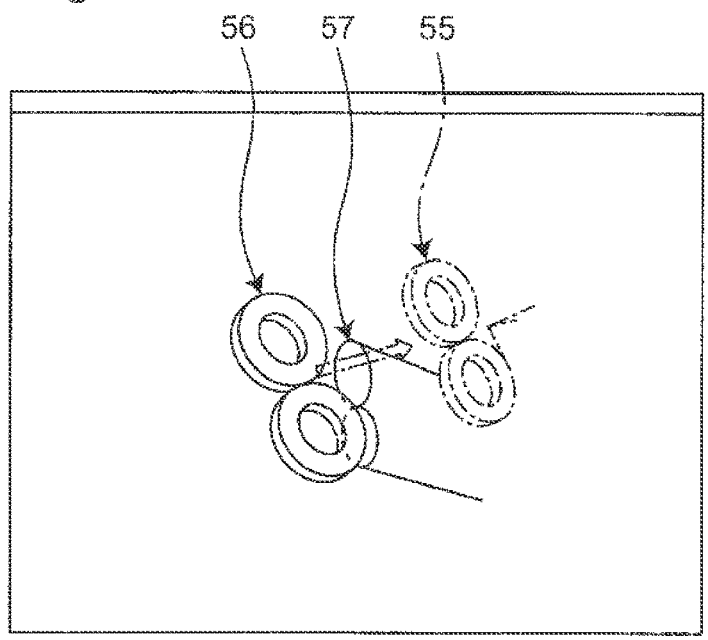
FIG. 4 is an explanatory diagram illustrating an image display example by a display device used in the embodiment.

In this embodiment, Open GL is installed as a program interface for graphic in order to display an image in the display device 28 so that, as shown in FIG. 4, a coil holder image 55 corresponding to the optimum stimulating position (alternate long and short dash line in FIG. 4) and a coil holder image 56 at the current position (solid line in FIG. 4) are displayed in the same screen. It should be noted that, more preferably, a sensor fixation member (glasses) image 57 is displayed in the same screen.

Therefore, the operator (user) of the coil holder 12 is only required to manipulate the coil holder 12 to displace along the scalp of the patient while watching the user interface section (display device) 28 such that the coil holder image 56 in a solid line (current position) displayed in the screen overlaps with the coil holder image 55 in an alternate long and short dash line (optimum stimulating position) as much as possible.

Figure 5:
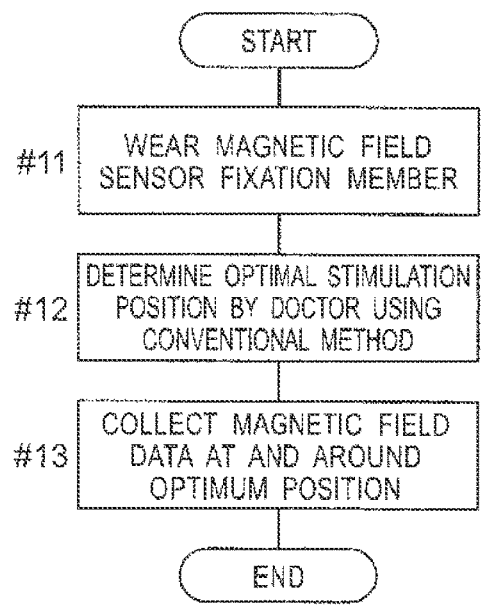
FIG. 5 is a flowchart explaining the operation method of the transcranial magnetic stimulator in an initial treatment in a hospital having specialized physicians.

An operation method of the electromagnetic stimulation device provided with the data set analyzing unit 20 thus configured is described with reference to flowcharts of FIG. 5 and FIG. 6.

First, in the initial treatment in the hospital (see FIG. 5), in step #11, the patient M wears the magnetic field sensor fixation member 14. Specifically, the patient M wears the pair of eyeglasses 14 having the plurality of magnetic field sensors 13 (for example, four, in this embodiment). Along with this, the detection signals are inputted to the signal analyzing section 22 from the plurality of the magnetic field sensors 13 (sensor 1, sensor 2, . . . , and sensor N) (see the arrow Y1 in FIG. 3). Then, the doctor determines the optimal stimulation position according to the conventional method while referring to a response of a muscle in a region where the patient M feels a pain (step #12). Thereafter, in step #13, the magnetic field data (sample magnetic field data) are collected for the optimal stimulation position and a plurality of (in this embodiment, on the order of 10) positions around the optimal position, and the sample magnetic field data is recorded in the recording section 23 of the data set analyzing unit 20.

Next, in the home treatment (see FIG. 6), similarly to the case of the treatment in the hospital, first, the patient M wears the magnetic field sensor fixation member 14 (step #21). Then, the user adjusts the magnetic coil 11 to the optimum position and posture as much as possible while watching the display in the user interface unit (display device) 28 (step #22), and the user manipulates to move the coil holder 12 while watching the display screen utilizing a navigating function of the user interface unit 28 of the data set analyzing unit 20, and guides the magnetic coil 11 to the optimal stimulation position and posture to perform the treatment (step #23). In other words, the manipulation of the magnetic coil 11 to displace is stopped at the position and posture of the magnetic coil 11 at this time, and this state is maintained. At this time, as described previously, it is convenient to fix the coil holder 12 using the holder fixation member 3 (see FIG. 1).

As described above, according to this embodiment, by utilizing the data sets, only by manipulating the coil holder 12 to displace such that the deviation provided by the user interface 28 becomes zero, the user of the electromagnetic stimulation device 10 can fairly easily detect the three-dimensional position and posture corresponding to the optimum position and posture of the magnetic coil 11 with which the magnetic stimulation is to be applied, without needing any special proficiency. Specifically, the patient M or the family member of the patient M, or a personal doctor in the neighborhood who is not necessarily specialized, can operate and use the stimulator fairly easily. Further, as it is not necessary to use a large-scale and expensive stimulator as conventionally required in order to detect the three-dimensional position and posture of the magnetic coil 11, the cost can be minimized, and it is easily possible to secure an installation space even in such as the patient's house, or a relatively small-scale doctor's office or clinic. Specifically, it is possible to provide the electromagnetic stimulation device 10 that can be easily handled and operated and is further downsized with lower cost, and this allows the patient M to perform the transcranial magnetic stimulation treatment continuously and repeatedly on a daily basis at home, the personal doctor's office in the neighborhood, or such.

In this case, the burden for the doctor involved in the conventional collection of data sets may be significantly reduced by performing a collecting operation of a large number of data sets (factory-produced data sets) separately from the collection of magnetic field data by the doctor in the hospital other than collection of a relatively smaller number of magnetic field data (sample magnetic field data) required for determination of the optimal stimulation position and posture.

It should be noted that in the above embodiment, the user interface unit 28 as the instructing means for providing the deviation of the three-dimensional data obtained by the data set analyzing unit 20 from the three-dimensional reference data is configured by the display device 28 having a liquid crystal type display panel that provides the deviation by the visual information. Instead, or in addition, it is possible to provide the deviation by auditory information using a loudspeaker and such. In this case, by configuring the instructing means to change at least one of a volume level, a musical scale, and a tone according to the magnitude of the deviation (the amount of displacement to be made by the coil holder 12), that is, as the stimulation coil 11 moves closer to the optimum position, it is possible to facilitate guidance to the optimum position and posture of the stimulation coil 11 and to further improve user-friendliness.

In this embodiment, in order to reduce the time required for guiding the magnetic coil when guiding the magnetic coil to the three-dimensional position and posture corresponding to the optimal stimulation position and posture utilizing the data sets, the magnetic coil is guided by extracting a data set within an appropriate range required for obtaining the three-dimensional position and posture of the magnetic coil corresponding to the optimal stimulation position and posture for an individual patient (hereinafter referred to as a "custom data set" for each patient) from an extremely large number of factory-produced data sets that have been collected, and by referring to the extracted custom dataset. Hereinafter, the method and such of extracting the custom data set will be described in detail.

Examples of the data set according to this embodiment are shown in Table 1. Pieces of the data indicated by additional characters 1 to n respectively correspond to data set numbers 1-n. Each magnetic field sensor measures values in three directions of x, y, and z, and therefore the magnetic field data is three-dimensional vectors, and the values in the corresponding directions are respectively shown with additional characters x, y, and z. Similarly, the position data is three-dimensional vectors, and values in the corresponding directions are respectively shown with additional characters x, y, and z. The posture data is also three-dimensional vectors, and a roll angle, a pitch angle, and yaw angle are respectively indicated by "roll", "pitch", and "yaw".

TABLE 1

| | Data Set | |
|---|---|---|
| No. | Position And Posture Of Coil | Magnetic Field (For Each Sensor) |
| 1 | $(x_1, y_1, z_1)$, $(roll_1, pitch_1, yaw_1,)$ | $(B_{1,1,x}, B_{1,1,y}, B_{1,1,z})$, $(B_{1,2,x}, B_{1,2,y}, B_{1,2,z})$, - - - |
| 2 | $(x_2, y_2, z_2)$, $(roll_2, pitch_2, yaw_2)$ | $(B_{2,1,x}, B_{2,1,y}, B_{2,1,z})$, $(B_{2,2,x}, B_{2,2,y}, B_{2,2,z})$, - - - |
| - - - | - - - | - - - |
| n | $(x_n, y_n, z_n)$, $(roll_n, pitch_n, yaw_n)$ | $(B_{n,1,x}, B_{n,1,y}, B_{n,1,z})$, $(B_{n,2,x}, B_{n,2,y}, B_{n,2,z})$, - - - |

Further, the CPU (Central Processing Unit) of the computer, the software, and such that are used in simulations carried out for generation of the factory-produced data sets according to this embodiment and discussion and confirmation are shown in Table 2.

TABLE 2

| | |
|---|---|
| OS | Microsoft Windows 7 |
| CPU | Dell Intel Core i7 CPU 860 |
| Clock Frequency | 2.80 GHz |

TABLE 2-continued

| Mounted Memory (RAM) | 4.00 GB (2.99 GB Available) |
| --- | --- |
| Used Language | C Language |
| Used Software | Microsoft Visual Studio 2008 |

[Preparation of Data Sets]
<Elements of Data Set>

As shown in Table 1, parameters that constitute a data set are x, y, z [m] representing the three-dimensional position of the magnetic coil, roll, pitch, yaw [rad] representing the posture of the magnetic coil, and direction components Bx, By, Bz [T] of the magnetic field sensed by each magnetic field sensor. The number of the magnetic field sensors is four, as described above. The three-dimensional position of the magnetic coil represented by x, y, and z is a position of a coil coordinate system origin illustrated in FIG. 8 with respect to a glass coordinate system taking a central position of height of lenses or a frame of the pair of eyeglasses 14 illustrated in FIG. 7 as an origin.

Roll, pitch, and yaw representing the posture of the magnetic coil 11 are angles of inclination of the coil coordinate system with respect to the glass coordinate system, and respectively correspond to rotation angles about a z axis, a y axis, and an x axis of the glass coordinate system. When a stimulation surface of the coil 11 faces straight downward, pitch=0 and yaw=0, and the stimulation surface of the coil 11 faces a direction of the surface of the scalp depends on the pitch and the yaw.

<Direct Analysis of Magnetic Field>

The magnetic field of the factory-produced data sets was generated by performing a direct analysis of the magnetic field for each of x, y, z, roll, pitch, and yaw of various types, and by performing calculation to each component of the magnetic field assumed to be sensed by each magnetic field sensor.

Figure 8:
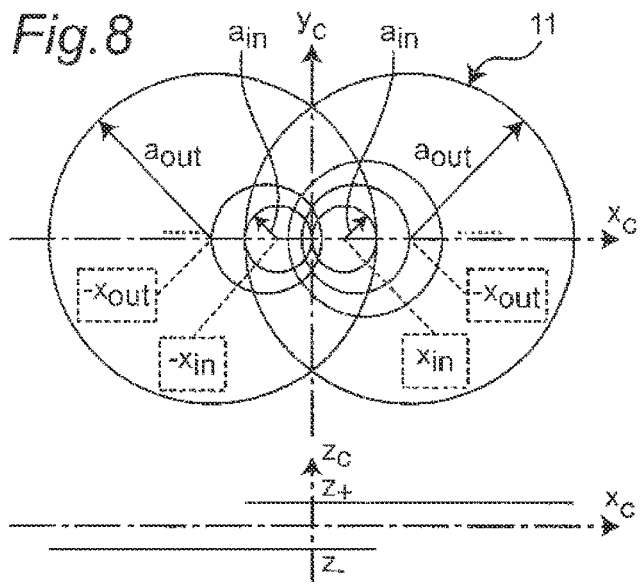
FIG. 8 is an explanatory diagram illustrating the magnetic coil and a coil coordinate system according to the embodiment.

As illustrated in FIG. 8, the shape of the magnetic coil is such that, using eccentric coils for both of the two spiral coils such that winding becomes dense in a direction corresponding to an intersection in the figure of eight, one of the two eccentric coils are placed on top of the other, and the position and the posture in the coil coordinate system with respect to the glass coordinate system are taken as the position and the posture of the coil. In this case, it is possible to produce an induction current more effectively immediately under a point corresponding to the intersection in the figure of eight.

Based on a ring current of radius $a_i$ and current I, a polygonal approximation solution of a magnetic field produced at a position (x, y, z) from the center of the ring is expressed by Expression 1. In the following, additional characters c and g of the vector respectively represents the coil coordinate system and the glass coordinate system.

Further, in Expression 1, it is assumed that $K=\mu_0 I/2N$, space permeability $\mu_0=4\pi \times 10^{-7}$ [H/m], the number of sides of the polygonal approximation N=36, the angle of sides in the polygonal approximation $\theta_n=2n\pi/N$, and the current through the coil I=4600 [A].

$$B_{i,c} = \begin{pmatrix} B_{x_i} \\ B_{y_i} \\ B_{z_i} \end{pmatrix} \quad \text{[Expression 1]}$$

$$= K_{a_i} \sum_{n=1}^{N} [(\bar{x} - a_i \cos\theta_n)^2 + (\bar{y} - a_i \sin\theta_n)^2 + \bar{z}^2]^{-\frac{3}{2}}$$

$$\begin{pmatrix} \bar{z}\cos\theta_n \\ \bar{z}\sin\theta_n \\ a_i - \bar{x}\cos\theta_n - \bar{y}\sin\theta_n \end{pmatrix}$$

Moreover, the ring radius $a_i$ is expressed by Expression 2, and a position of the magnetic field sensor ($s_c$) viewed from the ring center is expressed as in Expression 3 using a rotation matrix (R) using the ring center ($c_{i\pm, c}$), the sensor coordinate ($s_g$), and the posture of the coil on the data set roll=$\psi'$, pitch=$\theta'$, and yaw=$\varphi'$ in Expression 4, Expression 5, and Expression 6, and using the position of the coil on the data set ($p_g$=(x, y, z)). Here, the number of turns of the coil on one side K=10 (0≤i≤K-1). It should be noted that it is expressed as cos α=Cα, sin α=Sα in Expression 6.

$$a_i = a_{in} + i(a_{out} - a_{in})/(K-1),\ a_{in} = 0.02,\ a_{out} = 0.08 \quad \text{[Expression 2]}$$

$$\bar{s}_c = \begin{pmatrix} \bar{x} \\ \bar{y} \\ \bar{z} \end{pmatrix} = R^{-1}\{s_g - (p_g + R c_{i\pm,c})\} \quad \text{[Expression 3]}$$

$$c_{i\pm,c} = \begin{pmatrix} x_i \\ 0 \\ z_\pm \end{pmatrix} = \begin{pmatrix} x_0 + i(x_K - x_0)/(K-1) \\ 0 \\ \pm 0.005 \end{pmatrix}, \quad \text{[Expression 4]}$$

$$x_0 = 0.02,\ x_K = 0.06$$

$$s_g = \begin{pmatrix} 0.07 \\ 0.07 \\ 0 \end{pmatrix}, \begin{pmatrix} -0.07 \\ 0.07 \\ 0 \end{pmatrix}, \begin{pmatrix} -0.07 \\ -0.07 \\ 0 \end{pmatrix}, \begin{pmatrix} 0.07 \\ -0.07 \\ 0 \end{pmatrix} \quad \text{[Expression 5]}$$

$$R = \quad \text{[Expression 6]}$$
$$\begin{pmatrix} C\phi'C\theta' & S\phi'C\theta' & -S\theta' \\ C\phi'S\theta'S\psi' - S\phi'C\psi' & S\phi'S\theta'S\psi' + C\phi'C\psi' & C\theta'S\psi' \\ C\phi'S\theta'C\psi' + S\phi'S\psi' & S\phi'S\theta'C\psi' - C\phi'S\psi' & C\theta'C\psi' \end{pmatrix}$$

In this manner, after the sum of the magnetic fields produced from all of the rings for the magnetic field sensors 13 is taken and converted into the glass coordinate system using the rotation matrix (R), the magnetic field for each the magnetic field sensor 13 is obtained. It should be noted that as an inverse analysis of the magnetic fields produced by the coils may be performed with two or more of the magnetic field sensors 13, the magnetic field with respect to specific position and posture of the stimulation coil and vice versa are uniquely determined. Further, the positions of the magnetic field sensors 13 are determined based on a bizygomatic width and a mastoid pitch of an average human being (person).

<Pitch and Creation Range of Positions and Postures of Factory-Produced Data Sets>

The required accuracy for navigation is on the order of [mm] with respect to the position x, y, and z, and on the order of 5 [deg] with respect to the posture roll, pitch, and yaw. In order to achieve this accuracy, the pitch between the data sets is defined at intervals of 2.5 [mm] with respect to the position, and at intervals of 2.5 [deg] with respect to the posture.

Figure 9:
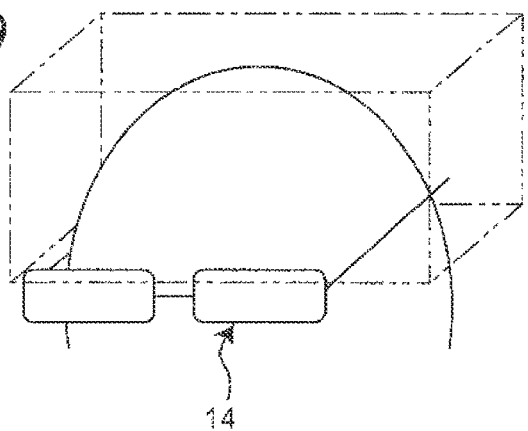
FIG. 9 is an explanatory diagram illustrating one example of a rectangular creation range of factory-produced data sets.

Regarding the creation range of the data sets, as shown by an alternate long and two short dashes line in FIG. 9, if any probable postures that the coil may take within an entire rectangle accommodating the size of a human head are included in a creation range, the creation range may possibly include a large number of data sets that are less necessary such as data sets within the head that is practically impossible as a data set, or of the coil spaced away from the head to a large extent of the stimulation surface or of the coil not facing the surface of the scalp. The number of the data sets is 81×97×61×144×144×72=357,778,363,392, when the creation range is set as follows.

Figure 10:
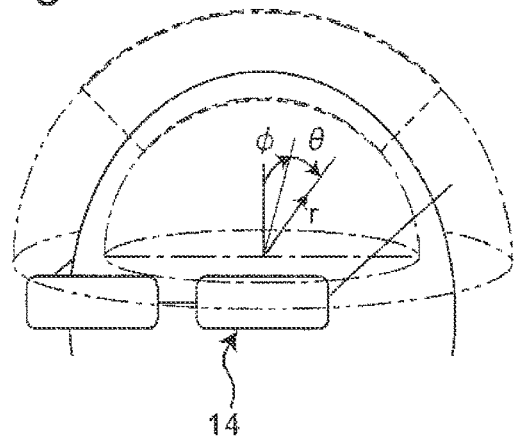
FIG. 10 is an explanatory diagram illustrating one example of a hemispherical creation range of factory-produced data sets.

$-0.1 \leq x \leq 0.1, -0.12 \leq y \leq 0.12, 0 \leq z \leq 0.15$ $-\pi \leq \text{roll} \leq \pi, -\pi \leq \text{pitch} \leq \pi, -\pi/2 \leq \text{yaw} \leq \pi/2$ On the other hand, as shown in FIG. 10, when the creation range is set so as to narrow down to apart of a sphere accommodating the size of a human head for the positions (see an alternate long and two short dashes line in FIG. 10), and, for the postures, to a range around angles at which the stimulation surface of the coil faces the surface of the scalp (see a dashed line in FIG. 10), it is possible to significantly reduce unnecessary data sets. In this embodiment, the creation range is set as follows, where $x = r \sin \theta$, $y = r \cos \theta \sin \varphi$, $z = r \cos \theta \cos \varphi$.

$0.085 \leq r \leq 0.105, -\pi/6 \leq \theta \leq \pi/6, -\pi/6 \leq \varphi \leq \pi/6$ $-\pi/6 \leq \text{roll} \leq \pi/6, \theta - \pi/6 \leq \text{pitch} \leq \theta + \pi/6,$ $\varphi - \pi/6 \leq \text{yaw} \leq \varphi + \pi/6$ It should be noted that the range of the roll is also limited considering the practical use in order to prevent the number of the data sets from excessively increasing too much, while it does not affect the fact whether or not the magnetic coil faces the surface of the scalp.

Figure 11:
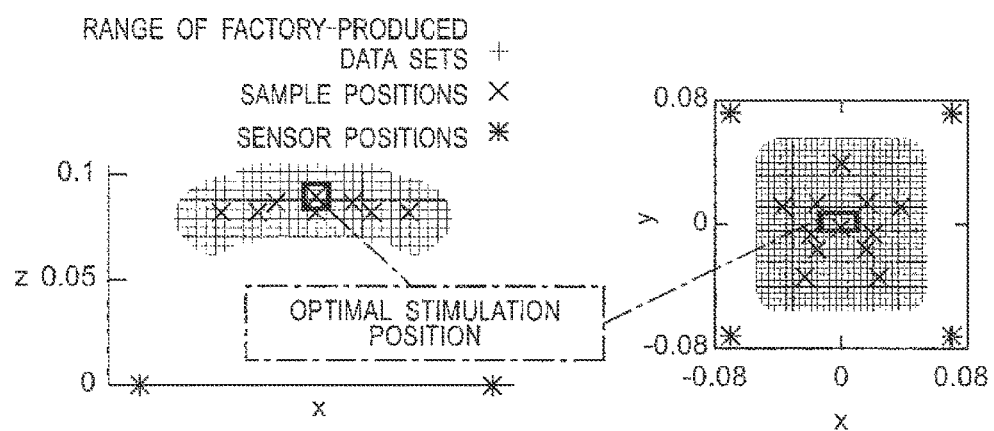
FIG. 11 is an explanatory diagram illustrating the creation range of factory-produced data sets, magnetic field sensors, and sample positions.

In actual generation of the factory-produced data sets, changing x, y, z, roll, pitch, and yaw at 2.5 [mm] and 2.5 [deg] intervals in a grid pattern, and only the data sets within the above creation range are considered and generated as the factory-produced data sets. The generated result is schematically shown in FIG. 11. It should be noted that the number of the data sets in this case is 174,425,400, which is ½₀₀₀ or smaller of that in the rectangular creation range.

It should be noted that as the "human (person's) head" in the generation of the factory-produced data sets, a head model representing a human head, for example, a head model based on a standard head structure of Japanese adults is used.

<Simulation Samples>

In this embodiment, simulations for discussion and confirmation for data set extraction are also performed other than the generation of the factory-produced data sets. In order to perform the simulations, simulation samples are prepared for sample magnetic field data collected by the doctor in the hospital. The sample magnetic field data is magnetic field information collected from the surface of the scalp of the patient, and therefore it is necessary that the position of each simulation sample is on the surface of the scalp, and the posture of each simulation sample is such that the stimulation surface of the coil faces a direction of a normal line of the surface of the scalp. In the simulations in this embodiment, the shape of the patient's head is assumed to be a spherical shape with the radius r=0.09 [m] centering the origin of the glass coordinate system, and the samples are selected from the factory-produced data sets based on this.

It should be noted that, unless otherwise stated, in the simulations in this embodiment, 10 pieces of the magnetic field information calculated from the positions and postures shown in common to Table 3 below and above described FIG. 11 are used as the sample magnetic field, and a sample No. 1 among these is taken as a sample with the optimal stimulation position and posture. It should be noted that Table 3 also shows a distance from the origin of the glass coordinate system $r = \sqrt{(x^2 + y^2 + z^2)}$, in order to show that the samples follow the shape of the patient's head. It can be seen that each sample has a value close to r=0.09 [m].

TABLE 3

Positions And Postures of Samples

| No. | x [m] | y [m] | z [m] | r [m] | roll [deg] | pitch [deg] | yaw [deg] |
|---|---|---|---|---|---|---|---|
| 1 | 0 | 0 | 0.09 | 0.090000 | 0 | 0 | 0 |
| 2 | −0.015 | −0.015 | 0.0875 | 0.090035 | 0 | −10 | −10 |
| 3 | 0.015 | −0.015 | 0.0875 | 0.090035 | 0 | 10 | −10 |
| 4 | −0.015 | 0.015 | 0.0875 | 0.090035 | 0 | −10 | 10 |
| 5 | 0.015 | 0.015 | 0.0875 | 0.090035 | 0 | 10 | 10 |
| 6 | 0 | 0.04 | 0.0825 | 0.091686 | 0 | 0 | 25 |
| 7 | −0.0375 | 0.0125 | 0.0825 | 0.091481 | 0 | −25 | 7.5 |
| 8 | 0.0375 | 0.0125 | 0.0825 | 0.091481 | 0 | 25 | 7.5 |
| 9 | −0.0225 | −0.0325 | 0.0825 | 0.091481 | 0 | −15 | −22.5 |
| 10 | 0.0225 | −0.0325 | 0.0825 | 0.091481 | 0 | 15 | −22.5 |

[Extraction Program]
<Flow of Data Set Extraction>

Figure 12:
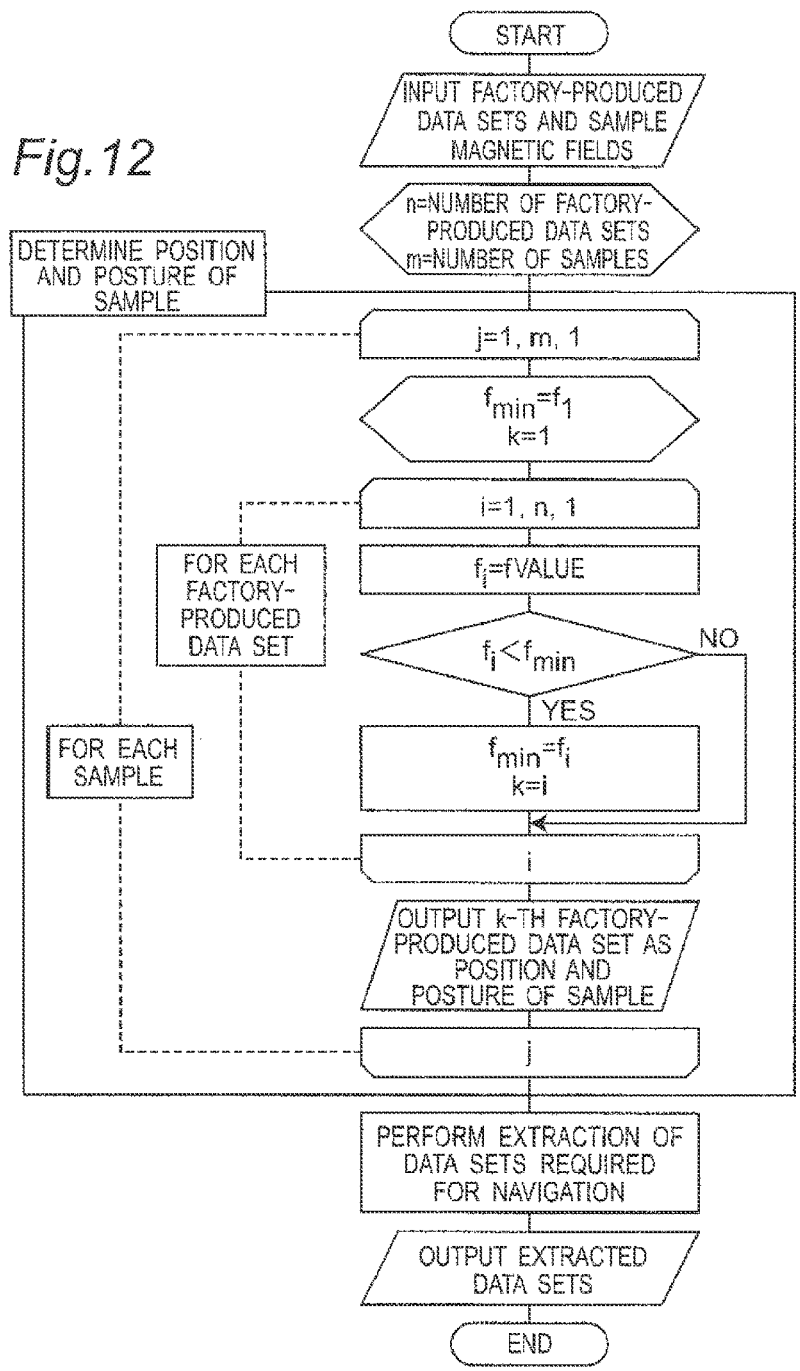
FIG. 12 is a flowchart for explaining an overall flow of a data set extraction procedure.

FIG. 12 shows a flow of extraction of the data sets. A factory-produced data set closest to the magnetic field information of a sample is searched, and the position and the posture of the sample are determined. With respect to the position and the posture, data sets whose position and the posture satisfy a certain condition with respect to the position and the posture are extracted from the factory-produced data sets as data sets for the patient.

<Method of Searching Factory-Produced Data Sets Whose Magnetic Field is Close to Samples>

FIG. 12 shows a procedure for determining the position and the posture of a sample. An f value in Expression 7 is used as a parameter for determining whether or not the magnetic field of the factory-produced data set is close to the magnetic field of the sample. The f value is a sum of squares of a difference of the components of the magnetic field, and the magnetic field of the sample and the magnetic field of the factory-produced data set are respectively represented by vector B ($B_1, B_2, \ldots, B_{12}$), vector $B'_i$ ($B'_{i1}, B'_{i2}, \ldots, B'_{i12}$) in Expression 7. It should be noted that direction components of all of vector B, $B'_i$,4 sensors representing the magnetic field are combined to provide twelve dimensions. For each sample, the f value is calculated for each of the factory-produced data sets, and one factory-produced data set whose f value taking a smallest value is selected. The position and the posture are taken as the position and the posture of the sample.

$$f_i = \|B - B'_i\|^2 \quad \text{[Expression 7]}$$

<Number of Extracted Data Sets>

The larger the number of the data sets used in the navigation, the more navigation accuracy is improved. However, if there are too many data sets, an amount of calculation increases and an operation of the system becomes slower, thus resulting in extension of time required for the navigation by that. Conventionally, in order to achieve the navigation accuracy on the order of 5 [mm] with respect to the position x, y, and z, and on the order of 5 [deg] with respect to the posture roll, pitch, and yaw as the navigation accuracy, at least about 500 data sets are required. However, a maximum number of data sets with which the navigation can be performed has not been known.

Thus, a simple experiment to find out the maximum number of data sets that can be handled was carried out. As a result of the system actually operating with varying numbers of the data sets of 1000, 2000, and 5000, the navigation was smoothly performed with 1000 and 2000. As a slight operating delay was observed when the number of the data sets increased up to 5000, it was determined that the navigation would be difficult with a number of data sets larger than this. Thus, in this embodiment, a maximum number of the extracted data sets is determined to be roughly 5000.

<Condition of Data Set Extraction>

In this embodiment, a simulation was performed mainly with changing conditions for the data set extraction, and the extracted data sets were evaluated for each extraction condition. The extracted data sets should be naturally suited for the navigation, but taking this as an only condition makes an objective obscure. Therefore, when determining the extraction conditions, certain standards as follows were set for the extracted data sets, and the extraction conditions were improved in every simulation to be closer to the standards as much as possible. The standards are as follows in order of priority:

(a) extracting data sets mainly at positions along the surface of the scalp and of postures with stimulation surface facing the surface of the scalp;

(b) extracting preferentially to data sets on the surface of the scalp over data sets within the scalp;

(c) extracting data sets densely near the optimal stimulation position and posture in order to ensure the navigation accuracy;

(d) extracting data sets evenly without an unintended and excessive difference in density other than the above; and (e) adding an extra condition to improve the navigation accuracy as needed.

[Extraction of Data Sets Near Position and Posture of Sample]

<Condition Setting>

Figure 13:
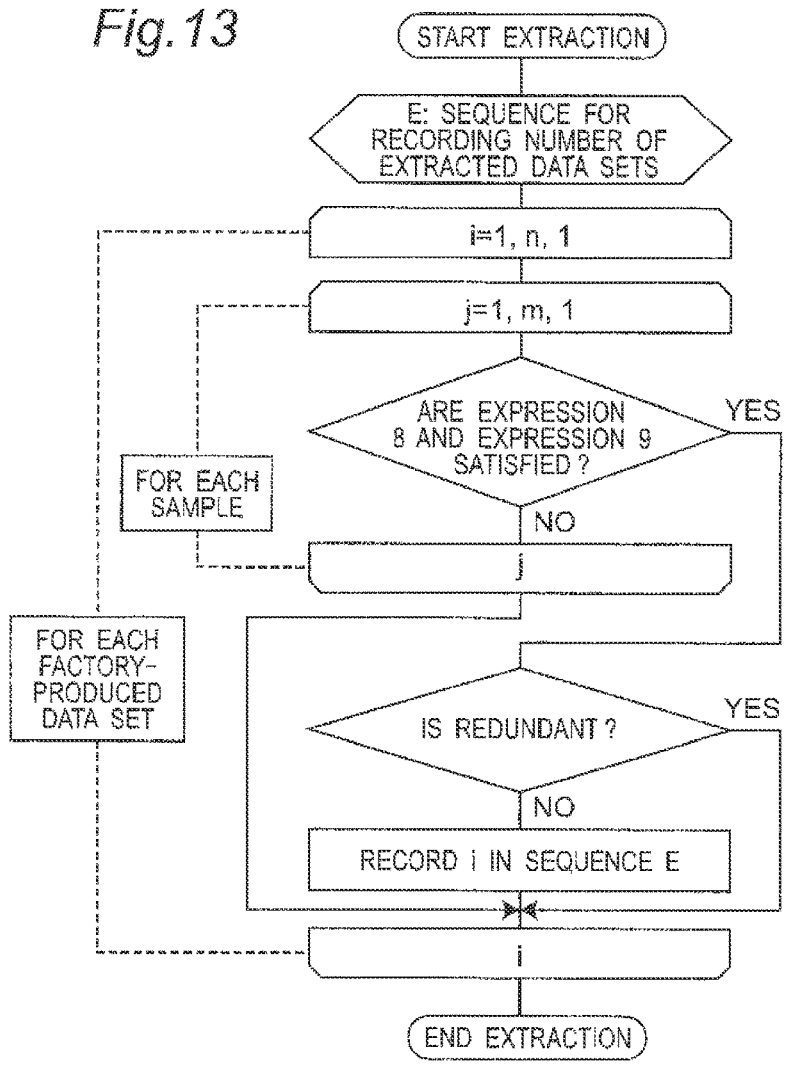
FIG. 13 is a flowchart for explaining a data set extraction procedure near the samples.

First, as a most simplest extraction condition, it was conceived to extract the factory-produced data sets whose distance from the three-dimensional position of the sample is equal to or shorter than a certain distance and having a posture closer to that of the sample. FIG. 13 shows a flow of selection of the extracted data sets, and extraction conditions are expressed by Expression 8 and Expression 9.

$$\|F_i - S_j\|^2 \leq P \quad \text{[Expression 8]}$$

$$|roll_i^{(f)} - roll_j^{(s)}| \leq A, |pitch_i^{(f)} - pitch_j^{(s)}| \leq A, |yaw_i^{(f)} - yaw_j^{(s)}| \leq A \quad \text{[Expression 9]}$$

Here, additional characters (f) and (s) respectively indicate the components of the factory-produced data set and the sample, additional characters i and j indicate the data set number, and the three-dimensional position of the factory-produced data set and the three-dimensional position of the sample are respectively expressed by Expression 10 and Expression 11. Further, P and A in Expression 8 and Expression 9 respectively indicate threshold values determining an extraction range of the positions and the postures; the extraction were performed changing these values in six ways as shown in Table 4 and the positions and the postures of the extracted data sets and the number of extraction were evaluated.

$$F_i(x_i^{(f)}, y_i^{(f)}, z_i^{(f)}) \quad \text{[Expression 10]}$$

$$S_j(x_j^{(s)}, y_j^{(s)}, z_j^{(s)}) \quad \text{[Expression 11]}$$

TABLE 4

Patterns Of Threshold Values Determining Extraction Range Assumed To Be Near Samples

| No. | P [m²] | A [rad] |
|---|---|---|
| 1 | $1.0 \times 10^{-4}$ | $\pi/144$ |
| 2 | $1.0 \times 10^{-4}$ | $\pi/72$ |
| 3 | $3.0 \times 10^{-5}$ | $\pi/144$ |
| 4 | $3.0 \times 10^{-5}$ | $\pi/72$ |
| 5 | $1.0 \times 10^{-5}$ | $\pi/144$ |
| 6 | $1.0 \times 10^{-5}$ | $\pi/72$ |

<Extraction Result>

Figure 14:
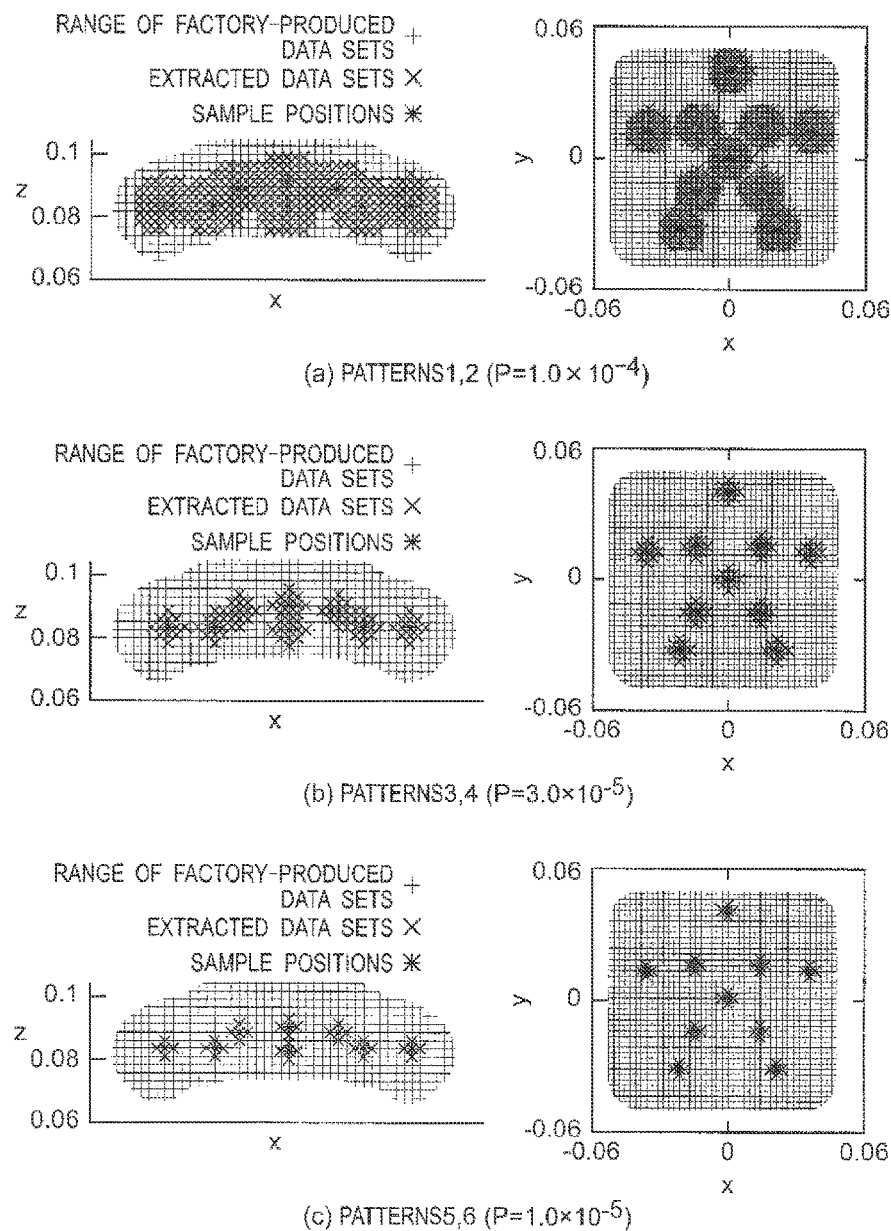
FIG. 14 shows explanatory diagrams illustrating data set extraction results near sample positions and postures.

FIG. 14 shows a diagram plotting the positions of the extracted data sets using a chart generation tool GNUPLOT. Further, the numbers of the extracted data sets are shown in Table 5.

TABLE 5

Numbers Of Data Sets When Extracting Near Positions And Postures Of Samples

| No. | Numbers Of Extraction |
|---|---|
| 1 | 2268 |
| 2 | 61236 |
| 3 | 330 |
| 4 | 8910 |
| 5 | 70 |
| 6 | 1890 |

Referring to Table 5, the data was actually extracted near each sample, and the navigation accuracy is ensured locally. However, the result is overly uneven, as there are no data sets regarding positions having no samples nearby. In addition, the number of the extracted data sets varies to a large extent only if the extraction range becomes larger by a small amount, as the parameters determining the position and the posture are three-dimensional. Further, considering a case of $P=1.0\times10^{-4}$, the number of the extracted data set is over 60000 when $A=\pi/72$ (the threshold value pattern No. 2 in Table 4), which is apparently beyond the number of data sets with which the navigation is possible. Moreover, for a case in which the number of data sets covering about a half of the surface of the scalp is 2000 or more when $A=\pi/144$ (the threshold value pattern No. 1 in Table 4), that is, when the extraction range is set fairly small so that only one posture is extracted for each position, this is also considered to involve a loss in extraction considering the fact that the current system is able to perform the navigation only with 500 data sets.

It is possible to extract necessary data sets efficiently when increasing the number of samples up to 40 or when limited to a small range, but this is hardly versatile. Further, when $P=3.0\times10^{-5}$ and $A=\pi/72$ (the threshold value pattern No. 4 in Table 4), it is not possible to reduce the number of data sets to 5000 or smaller as the number of the extracted data sets is 8910.

From the above results, in this embodiment, instead of setting an extraction condition for each sample, the shape of the surface of the scalp is estimated based on the all samples, and the data sets along its surface are extracted.

[Extraction of Data Sets Along Surface of Approximation Scalp]

<Delaunay Triangulation>

First, a method of estimating the shape of the surface of the scalp based on the samples is described. The actual surface of the scalp is constituted by a curve of which mathematization is difficult, and its shape varies from person to person. However, this curve is not very complicated nor markedly uneven, and it is possible approximate using a simple figure. Therefore, as a method of approximating to the surface of the scalp by connecting points of the samples to generate a plurality of triangles, so-called Delaunay triangulation is used.

Delaunay triangulation is a method of dividing into a group of triangles as small as possible taking a set of points as apices such that an inner angle of a smallest one of all triangles is maximum. There is a geometric nature that a circumcircle of triangles resulting from the triangulation by this method does not include other apices. This method of dividing is suitable for approximation of a curve of a relatively simple shape that is not overly uneven, as an elongated triangle is less easily generated.

Considering an application of Delaunay triangulation to this embodiment, as a change in z is small as compared to changes in x and y out of the three-dimensional position of the samples, the shape of the surface of the scalp was approximated to a plurality of triangles by determining whether or not the condition of Delaunay triangulation is satisfied two-dimensionally using only x and y, and generating triangles three-dimensionally using x, y, and z.

According to a program used in this embodiment, Delaunay triangulation was carried out based on the following algorithm.

First, any three points are selected from the samples, and its circumcenter and circumcircle radius are obtained. A distance from each of the remaining samples other than the selected three points to the circumcenter is compared with the circumcircle radius, and if the circumcircle radius is smaller than the distance for all of the samples, the selected three points are considered to form a triangle that constitutes Delaunay triangulation. The above is performed to each combination of three points.

A circumcenter of a triangle whose positions of apices are known may be obtained in the following manner.

For ΔOAB illustrated in FIG. 15, Expression 13 and Expression 14 may be established, where a vector OA=a vector (a), a vector OB=a vector (b), an absolute value of the vector (a)=a, an absolute value of the vector (b)=b, and an angle AOB=θ, points Q and R are taken respectively such that a vector OQ=X(a) and a vector OR=Y(b), a circumcenter P is expressed by Expression 12, and intersections between a side OA and a perpendicular line from a circumcenter P, and between a side OB and a perpendicular line from the circumcenter P are respectively C and D. Further, Expression 15 and Expression 16 are derived using these expressions. From the above, coefficients X and Y may be obtained from Expression 19 using Expression 17 and Expression 18. Then, coordinates of a circumcenter P may be obtained from coordinates of a point O by substituting Expression 19 into Expression 12.

$$\overrightarrow{OP} = \overrightarrow{OQ} + \overrightarrow{OR} = Xa + Yb \qquad \text{[Expression 12]}$$

$$\overrightarrow{OP} \cdot \overrightarrow{OA} = (Xa + Yb) \cdot a = Xa^2 + Yab\cos\theta \qquad \text{[Expression 13]}$$

$$\overrightarrow{OP} \cdot \overrightarrow{OB} = (Xa + Yb) \cdot b = Xab\cos\theta + Yb^2 \qquad \text{[Expression 14]}$$

$$\overrightarrow{OC} = \frac{\overrightarrow{OP} \cdot \overrightarrow{OA}}{|\overrightarrow{OA}|^2}\overrightarrow{OA} = \left(X + \frac{Yb\cos\theta}{a}\right)a = a/2 \qquad \text{[Expression 15]}$$

$$\overrightarrow{OD} = \frac{\overrightarrow{OP} \cdot \overrightarrow{OB}}{|\overrightarrow{OB}|^2}\overrightarrow{OB} = \left(\frac{Xa\cos\theta}{b} + Y\right)b = b/2 \qquad \text{[Expression 16]}$$

$$|\overrightarrow{CQ}| = Yb\cos\theta \qquad \text{[Expression 17]}$$

$$|\overrightarrow{DR}| = Xa\cos\theta \qquad \text{[Expression 18]}$$

$$X = \frac{(b - a\cos\theta)\cos\theta}{a\sin\theta^2}, Y = -\frac{(a - b\cos\theta)\cos\theta}{b\sin\theta^2} \qquad \text{[Expression 19]}$$

It should be noted that occasionally, there is a case in which there are 4 or more samples concyclically along the same circle and the circle does not include any other samples. In this case, the definition of Delaunay triangulation is maintained as a minimum inner angle is constant regardless of the triangle resulting from the triangulation. Therefore, in this embodiment, exceptionally as illustrated in FIG. 16, scanning was performed in a counterclockwise manner starting from a certain point along a circle, numbers 1, 2, 3, . . . were assigned to the samples in order of detection, and division into triangles such as (1, 2, 3), (1, 3, 4), (1, 4, 5), . . . was performed.

Further, FIG. 17 shows a result of Delaunay triangulation performed to the 10 samples commonly used in this embodiment (see Table 3). As illustrated in FIG. 17(*a*), it can be seen that lower four out of the 10 points (the sample No. 2, 3, 9, and 10 in Table 3) are concyclically along the same circle, and the triangulation is correctly performed to these points. Moreover, FIG. 17(*b*) is a diagram three-dimensionally showing the triangles resulting from the triangulation, and shows that the triangles follow the shape of an imaginary patient's head that is defined in the generation of the samples (that is, the head model representing the human head) to some extent. It should be noted that it was confirmed that Delaunay triangulation can be performed using the same program without any problem even if the number of samples is 40.

<Extraction of Data Sets Near Triangle Plane>

Next, a method of extracting data sets on a triangle plane of a triangle resulting from Delaunay triangulation will be explained.

Figure 18:
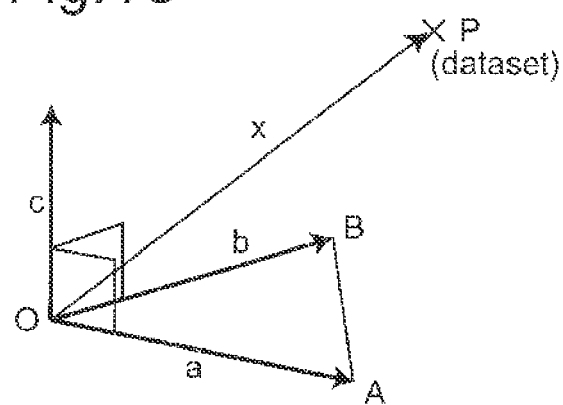
FIG. 18 is an explanatory diagram of parameters representing a position of a data set with respect to a triangle.

For ΔOAB illustrated in FIG. 18, it is assumed that the vector OA=the vector (a), the vector OB=the vector (b), a normal unit vector of ΔOAB in positive z direction is a vector (c), a position of a factory-produced data set is a point P, and a vector OP=vector (x). For each factory-produced data set, the vector x is resolved into components of the vectors (a), (b), and (c) as expressed in Expression 20. In Expression 20, the coefficients a and b are non-dimensional, as being ratios to the lengths of the side OA and the side OB, respectively, and a unit of the coefficient c is [m], as being a ratio to the normal unit vector (c).

$$x = aa + bb + cc \qquad \text{[Expression 20]}$$

Here, taking one factory-produced data set as an example, if the coefficients a and b satisfy Expression 21, this factory-produced data set is present immediately above ΔOAB. Further, it is considered that the smaller an absolute value of the coefficient c is, the closer to ΔOAB a position of this factory-produced data set is, and that this factory-produced data set is within the head if c<0, and over the head if c>0.

$$0 \le a \le 1, 0 \le b \le 1, 0 \le a+b \le 1 \qquad \text{[Expression 21]}$$

In the actual program, the coefficients a, b, and c were obtained by Gaussian elimination, and the extraction was performed so as to meet the following condition. The condition for the coefficients a and b is as follows.

Figure 19:
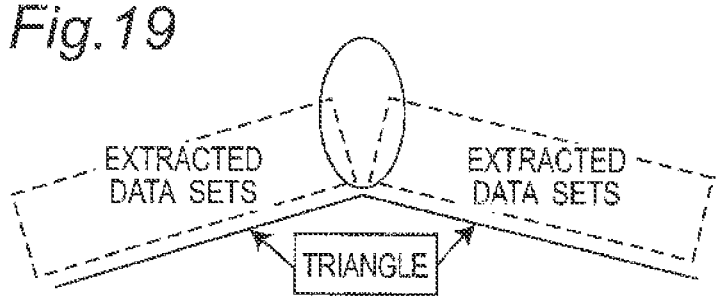
FIG. 19 is an explanatory diagram illustrating a blind area of data set extraction.

As the group of triangles that is handled is approximated to the surface of the scalp, the triangles are adjacent in a manner convex upward. Therefore, when extracting the data sets based on the condition of Expression 21, a blind area of extraction along the side of the triangle is produced as shown as an ellipse by a sold line in FIG. 19. In order to avoid this, as expressed by Expression 22, the extraction range was expanded by determining a threshold value R.

$$-R \le a \le 1+R, -R \le b \le 1+R, -R \le a+b \le 1+R \qquad \text{[Expression 22]}$$

Here, when the threshold value R=0, Expression 21 becomes equal to Expression 20, and if the threshold value R is increased, the extraction range is expanded in proportion. In this embodiment, it was basically assumed the threshold value R=0.1.

For the coefficient c, the simulation was performed while changing the condition while extracting c≥0 was satisfied and c was small. First, a threshold value W was given, and data sets satisfying 0≤c≤W were extracted. As a result of actual data set extraction to a single triangle taking the threshold values as R=0 and W=0.003 [m], it was confirmed that data sets immediately above the triangle were extracted.

<Condition Setting>

As described above, by approximating the surface of the scalp into plurality of triangles by Delaunay triangulation, and extracting the factory-produced data sets that are close to each of triangle planes that have been obtained, it becomes possible to extract the data sets near the surface of the scalp.

Figure 21:
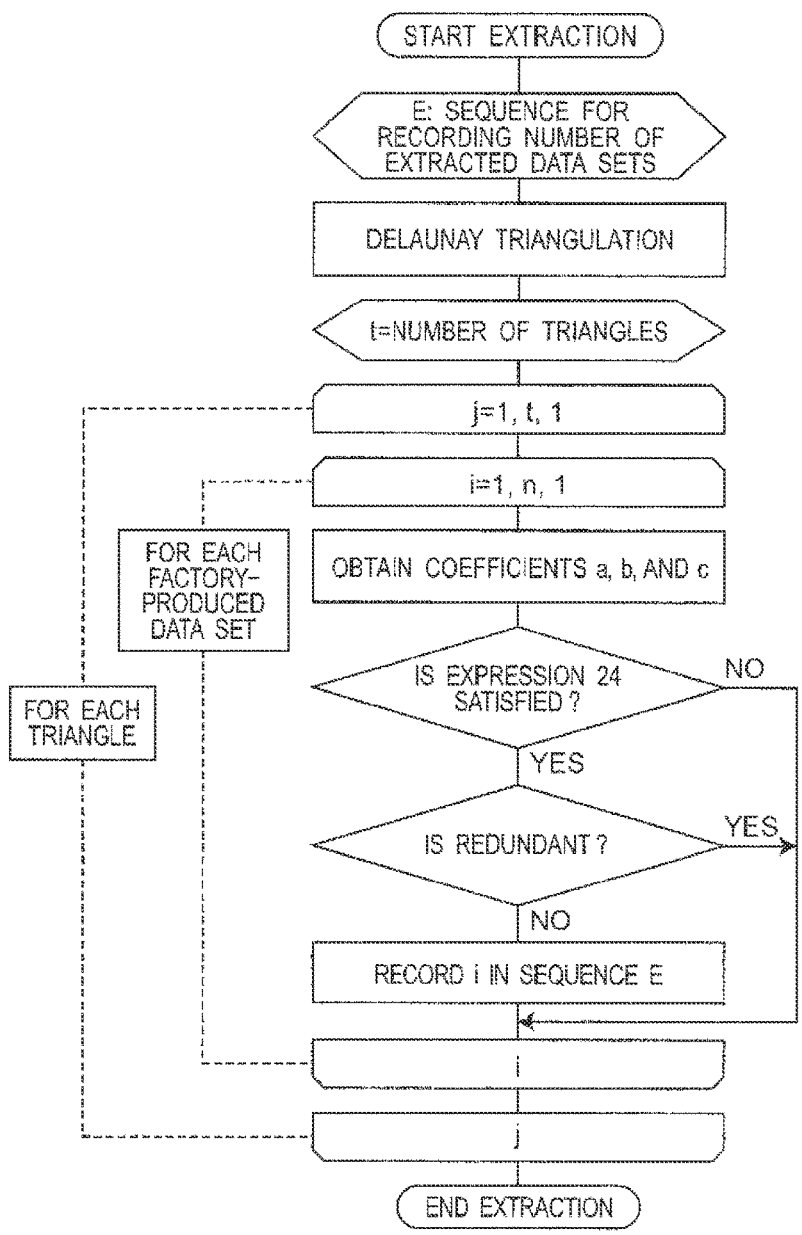
FIG. 21 is a flowchart for explaining a data set extraction procedure near an approximate surface of a scalp based on Delaunay triangulation.

Next, a case in which the extraction conditions are changed on the premise that this method is mainly used will be described. FIG. 21 shows a flow of selection of the extracted data sets. First, the condition relating to the position is that the threshold value W of the parameter c representing the distance from a triangle resulting from the triangulation is determined, and the factory-produced data sets satisfying this are extract.

Figure 20:
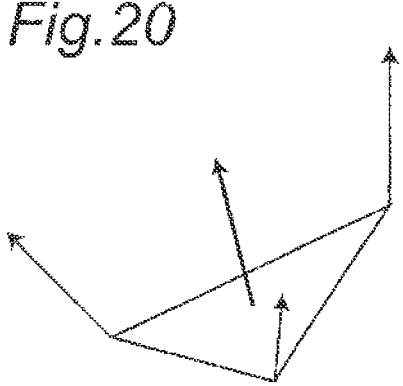
FIG. 20 is an explanatory diagram illustrating an average value of postures of three samples constituting a triangle resulting from the triangulation.

The condition relating to the posture is Expression 23, Expression 24, and that by taking an average value of postures of three samples constituting a triangle resulting from the triangulation as shown by FIG. 20, and providing the threshold value A, the factory-produced data sets whose posture is close to the posture of the average value are extracted. In Expression 23 and Expression 24, the additional characters (f), (s), and (a) respectively represent the factory-produced data sets, the samples, and the average of the three samples that constitute a triangle resulting from the triangulation, i represents a factory-produced data set number, j represents the number of the triangle resulting from the triangulation, and a number after j represents the number of an apex in the triangle.

$$\begin{cases} \text{roll}_j^{(a)} = (\text{roll}_{j1}^{(s)} + \text{roll}_{j2}^{(s)} + \text{roll}_{j3}^{(s)})/3 \\ \text{pitch}_j^{(a)} = (\text{pitch}_{j1}^{(s)} + \text{pitch}_{j2}^{(s)} + \text{pitch}_{j3}^{(s)})/3 \\ \text{yaw}_j^{(a)} = (\text{yaw}_{j1}^{(s)} + \text{yaw}_{j2}^{(s)} + \text{yaw}_{j3}^{(s)})/3 \end{cases} \qquad \text{[Expression 23]}$$

$$|\text{roll}_i^{(f)} - \text{roll}_j^{(a)}| \le A, |\text{pitch}_i^{(f)} - \text{pitch}_j^{(a)}| \le A, |\text{yaw}_i^{(f)} - \text{yaw}_j^{(a)}| \le A \qquad \text{[Expression 24]}$$

As described above, since expanding the extraction range relating to the posture by a small amount increases the number of the extracted data sets to a large extent, the postures were not evaluated in the simulation based on this condition, and the threshold value A is fixed to A=π/144 so that only one posture is extracted for each position as shown in Table 6. Accordingly, a target number of the extracted data sets was roughly 500 against 5000 as final goal. The value of the threshold value W was changed in three ways of single time, half times, and quarter times with respect to an interval between the data sets 2.5 [mm]. Based on these conditions, the positions and the numbers of the extracted data sets were evaluated for each trial.

TABLE 6

Patterns Of Threshold Values Determining Extraction Range Assumed To Be Near Surface Of Approximation Scalp

| No. | W [mm] | W/2.5 | A [rad] |
|---|---|---|---|
| 1 | 2.5 | 1 | π/144 |
| 2 | 1.25 | 1/2 | π/144 |
| 3 | 0.625 | 1/4 | π/144 |

<Extraction Result>

Figure 22:
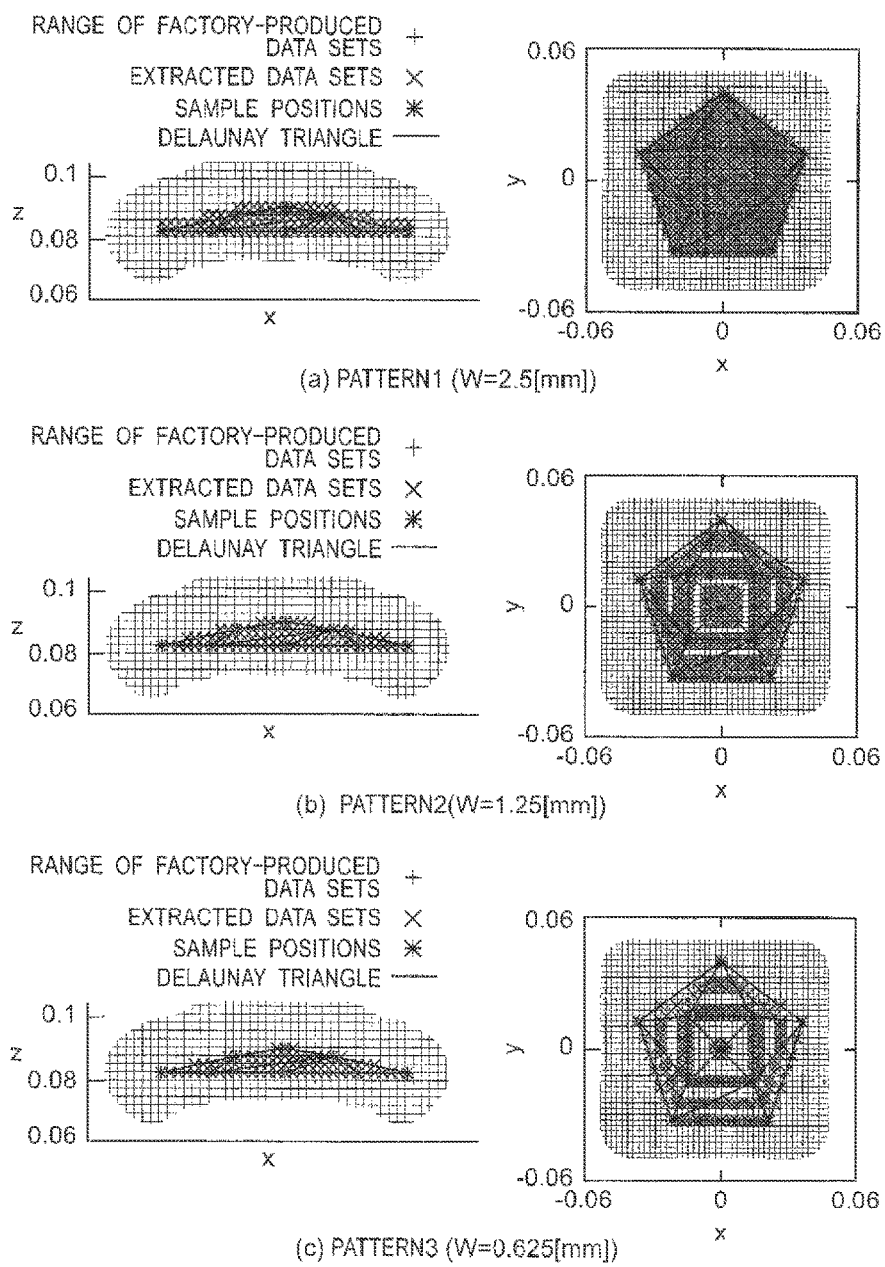
FIG. 22 shows explanatory diagrams illustrating data set extraction results near the approximate surface of the scalp.

FIG. 22 shows a diagram plotting the positions of the extracted data sets using the chart generation tool GNUPLOT. Further, FIG. 23 shows the distribution of the extracted data sets when taking a pattern 1, that is, when the threshold value W=2.5 [mm].

FIG. 23(*a*) shows a chart grouping the extracted data sets by the value of r in order to confirm whether or not the data sets along the surface of the scalp of the imaginary patient are extracted, while the shape of the surface of the scalp of an imaginary patient (that is, the human head model) is taken as the sphere centering the origin of the glass coordinate system with the radius $r=\sqrt{(x^2+y^2+z^2)}=0.09$ [m] as described above. A vertical axis represents the number of the extracted data sets, and a horizontal axis represents r. From the figure, it can be seen that only the data sets near r=0.09 [m] are extracted, and more data sets are extracted on an outer side of the surface of the scalp where the value of r is larger.

FIG. 23(*b*) shows a chart grouping the extracted data sets by the distance from the optimal stimulation position. A vertical axis represents the number of the extracted data sets, and a horizontal axis represents the distance from the optimal stimulation position. From the figure, it cannot be said that more data sets are extracted near the optimal stimulation position. However, this is not considered to be very comparable as a cubic volume of a target range decreases on the order of cube of the distance as the distance from the optimal stimulation position becomes smaller, and a chart in which a vertical axis represents an extraction density obtained by dividing the number of the extracted data sets by the cubic volume of the target range is prepared as FIG. 23(*c*). From this figure, it can be seen that somewhat more data sets are extracted near the optimal stimulation position. Along with the results shown in FIG. 22, a difference from the extraction result shown in FIG. 14 is very obvious, and it was confirmed that the extraction of the data sets along the surface of the scalp approximated by Delaunay triangulation is very effective.

Figure 24:
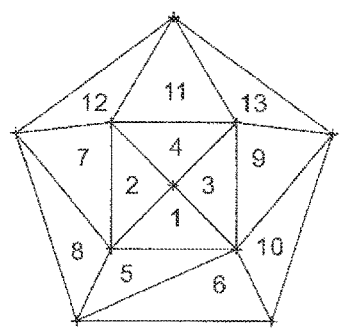
FIG. 24 is an explanatory diagram illustrating numbers and positions of triangles resulting from Delaunay triangulation to 10 samples.

However, this also involves the following problem. As illustrated in FIG. 22(*a*), if the width of the threshold value W is taken as wide as the interval between the data sets, it is possible to cover the surface of the approximation scalp as a whole by the extracted data sets. However, as shown in Table 7, the number of the extracted data sets slightly increases. If the width of the threshold value W is set narrower as in FIG. 22(*b*) and FIG. 22(*c*), it is possible to reduce the number of the extracted data sets. However, the positions of the extracted data sets gathers around a certain side or apex of the triangles instead of becoming evenly thin, or the number of the extracted data sets extremely reduces depending on a triangle. The disproportionality of the extracted data sets is considered to be produced because while the factory-produced data sets are arranged in a grid pattern in the x, y, and z axis directions, the surfaces of the triangles obliquely cross in a lattice direction. This is why the number of the extraction for triangle Nos. 12 and 13 decreased in each trial, and when W is small, the extraction is performed in stripes or the extraction result gathers around a specific side or apex. In Table 7, triangle Nos. are numbers based on reference numbers shown in FIG. 24.

in the x, y, and z axis directions, and therefore D in Expression 25 always takes an integer. Addition of a condition that D extracts only an even number of data sets is considered. With this, the extracted data sets gathering around a specific side or apex may be reduced to half evenly, and an amount of reduction of the extraction may be used for the extraction of other data sets.

$$D = \frac{x + y + z}{0.0025}$$ [Expression 25]

TABLE 7

Number Of Extracted Data Sets For Each Triangle

| Triangle No. | Apices Of Triangle | Area [mm²] | Pattern 1 | | Pattern 2 | | Pattern 3 | |
|---|---|---|---|---|---|---|---|---|
| | | | Number Of Extraction | Extraction Density [/mm²] | Number Of Extraction | Extraction Density [/mm²] | Number Of Extraction | Extraction Density [/mm²] |
| 1 | 1, 2, 3 | 228.1 | 58 | 0.2543 | 29 | 0.1271 | 17 | 0.0745 |
| 2 | 1, 2, 4 | 228.1 | 58 | 0.2543 | 29 | 0.1271 | 17 | 0.0745 |
| 3 | 1, 3, 5 | 228.1 | 58 | 0.2543 | 29 | 0.1271 | 17 | 0.0745 |
| 4 | 1, 4, 5 | 228.1 | 58 | 0.2543 | 29 | 0.1271 | 17 | 0.0745 |
| 5 | 2, 3, 9 | 273.0 | 54 | 0.1978 | 34 | 0.1245 | 19 | 0.0696 |
| 6 | 3, 9, 10 | 409.5 | 92 | 0.2247 | 46 | 0.1123 | 30 | 0.0733 |
| 7 | 2, 4, 7 | 345.7 | 65 | 0.1880 | 44 | 0.1273 | 31 | 0.0897 |
| 8 | 2, 7, 9 | 322.6 | 61 | 0.1891 | 31 | 0.0961 | 20 | 0.0620 |
| 9 | 3, 5, 8 | 345.7 | 65 | 0.1880 | 44 | 0.1273 | 31 | 0.0897 |
| 10 | 3, 8, 10 | 322.6 | 61 | 0.1891 | 31 | 0.0961 | 20 | 0.0620 |
| 11 | 4, 5, 6 | 382.4 | 77 | 0.2014 | 49 | 0.1281 | 37 | 0.0968 |
| 12 | 4, 6, 7 | 287.1 | 51 | 0.1776 | 23 | 0.0801 | 12 | 0.0418 |
| 13 | 5, 6, 8 | 287.1 | 51 | 0.1776 | 23 | 0.0801 | 12 | 0.0418 |
| Total | | 3888.1 | 809 | 0.2081 | 441 | 0.1134 | 280 | 0.0720 |

From the above result, based on the conditions for ideal extracted data sets considered in <Data Set Extraction Condition>, the following new extraction conditions were considered. However, the basic method of using Delaunay triangulation to the samples to approximate the surface of the scalp and extracting data sets on the surface is not changed. First, in order to prevent a difference from occurring in the number of the extracted data sets due to an orientation of a surface of a triangle, it is conceived that the constant number of data sets are extracted in ascending order of the distance c between the triangle and each factory-produced data set instead of providing the threshold value W. With this, the number of the extracted data sets and the extraction density of a specific triangle may not be extremely reduced at least. Further, in order to prevent the extraction result from gathering around a specific side or apex, a numeric condition that is not related to the extraction conditions considered so far is added. With this, it is possible to reduce the extraction result gathering around a specific side or apex, as well as to reduce disproportionality of the extracted data sets because the number of the extracted data sets fixedly reduced may be used for the extraction of data sets at other positions as described above.

[Extraction of Data Sets when Density Adjustment is Performed]
—Density Adjustment and Condition Setting—
<Dispersion of Data Sets>

The numeric extraction condition as listed below is added in order to prevent the extraction result from gathering around a specific side or apex. The factory-produced data sets are arranged at intervals of 0.0025 [m] in a grid pattern <Preferential Extraction of Data Sets Near Optimal Stimulation Position and Posture>

While the above method allows dispersion of the disproportional extracted data sets, this only reduces the number of the factory-produced data sets to be extracted to half, and makes the preparation of the factory-produced data sets at intervals of 2.5 [mm] pointless, and the navigation accuracy decreases. Accordingly, it was conceived to preferentially perform the extraction of the data sets to the positions near the optimal stimulation position and posture.

An extraction condition relating to the position is expressed by Expression 28 and Expression 29. Here, the additional characters (f) and (o) in Expression 28 and Expression 29 respectively represent the factory-produced data sets and the optimal stimulation position and posture, and the additional character i represents the number of the factory-produced data set. Further, the three-dimensional position of the factory-produced data sets and the optimal stimulation position are respectively expressed by Expression 26 and Expression 27.

For the position, the condition used in "extraction of data sets near position and posture of sample" described above is applied only to the sample No. 1 to be the optimal stimulation position and posture. As expressed in Expression 28, it is assumed that the threshold value P=0.0025 such that the extraction is performed for a single lattice in the directions of x, y, and z, and as expressed in Expression 29, the extraction is not performed for the data sets present in a negative z direction, that is, within the scalp. Specifically, for the position, the extraction was performed at total six points at, above, in front of, in the rear of, on the left of, and on the right of the optimal stimulation position.

$$F_i(x_i^{(f)}, y_i^{(f)}, z_i^{(f)}) \quad \text{[Expression 26]}$$

$$O(x^{(o)}, y^{(o)}, z^{(o)}) \quad \text{[Expression 27]}$$

$$\|F_i - O\|^2 \le P, P = 0.0025^2 \quad \text{[Expression 28]}$$

$$z_i^{(f)} - z^{(o)} \le 0 \quad \text{[Expression 29]}$$

Further, an extraction condition relating to the posture is expressed by Expression 30. For the posture, a small experimentation was carried out for setting the extraction condition. Specifically, the magnetic coil was applied to the top of the head model, and inclined little by little, and at this time, it was confirmed that a degree of inclination at which the fact that the coil stimulation surface did not face the surface of the scalp direction was obvious. As a result, it was confirmed that the fact that coil stimulation surface does not face the surface of the scalp direction was obvious at an inclination of 15 [deg] or greater. Accordingly, it was determined that data sets having a posture inclined more than this are less likely required. Then, the preferential extraction near the optimal stimulation posture was determined to be within a range of ±15 [deg] from the optimal stimulation posture. It should be noted that the inclination of the magnetic coil was measured using a known angle meter fixed with respect to this coil. In this manner, data for the inclination of the magnetic coil may be obtained using a known inclination measuring instrument such as an angle meter, a known inclination sensor, or the like.

However, the factory-produced data sets take postures by 2.5 [deg] for each of the roll, pitch, and yaw component, that is, 13 stages within the range of ±15 [deg]. Accordingly, if the extraction of all the data sets within this range is performed, the number of the extracted data sets is 6×13³=13182, which is well over 5000 as the target number of the number of the extracted data sets, only near the optimal stimulation position and posture. Therefore, as expressed in Expression 30, the extraction of each component is limited to 7 stages of 0, ±2.5, ±7.5, and ±15 [deg].

In practice, if the user notices there is an inclination to a certain direction from the optimal stimulation posture, the user attempts to correct the inclination, but a specific degree of inclination is not very important for the user. Therefore, in order to determine whether or not there is an inclination, data sets at 0 and ±2.5 [deg] are extracted, and the data sets at ±7.5 and ±15 [deg] are extracted in case that the inclination is slightly larger. With this, the number of the extracted data sets near the optimal stimulation position and posture becomes 6×7³=2058. It should be noted that while a case of 9 or more stages is also discussed, in this case, the number of the extracted data sets is 6×9³=4374 at minimum, and substantially reaches 5000, the extraction at the optimal stimulation posture is determined to be 7 stages for each component.

$$|\text{roll}_i^{(f)} - \text{roll}^{(o)}|, |\text{pitch}_i^{(f)} - \text{pitch}^{(o)}|, |\text{yaw}_i^{(f)} - \text{yaw}^{(o)}| = 0, 2.5, 7.5, 15 [\text{deg}] \quad \text{[Expression 30]}$$

<Fixation of Number of Extracted Data Sets>

In order to eliminate disproportionality of in the number of the extracted data sets for each triangle, which was the problem in the trial result described above, it is switched to the method of extracting the constant number of data sets in ascending order of the parameter c instead of providing the threshold value. With this, the following benefits are obtained.

Unintended disproportionality in the number of the extracted data sets between triangles may be eliminated.

The number of the extracted data sets may be fixed no matter what condition (for such as the posture) is set.

Density may be adjusted freely by adjusting the number of the extracted data sets for each triangle.

The total number of the extracted data sets is set to be 5000 as described above, and first, the extraction of the 2058 data sets near the optimal stimulation position and posture as described with reference to Expression 30 is performed, and the remaining 2942 data sets are divided into the triangles to determine the number of the extracted data sets for each triangle.

In the actual program, a process in which the threshold value W was set slightly larger, data sets satisfying the condition were sorted in ascending order of the parameter c using a quick sort method, and the constant number of data sets were extracted from a top of the arrangement was performed. The quick sort method is an unstable sort so to speak, where an order of elements to be sorted having the same value is not constant. However, this method whose average processing time is shortest is employed as there is no problem in using it in the data set extraction. Further, in order to adjust the density such that the closer the triangle is to the optimal stimulation position, the more the number of the extracted data sets increases, the number of the extracted data sets for each triangle is distributed to be proportional to an area of the triangle and reverse proportional to the distance between the optimal stimulation position and the barycenter.

<Extraction Condition Relating to Posture>

By fixing the number of the extracted data sets using the method described above, changing the extraction condition relating to the posture does not affect the number of the extracted data sets. Therefore, the extraction condition relating to the posture that has not been discussed much is considered.

As described above, whether or not the magnetic coil faces the surface of the scalp direction depends on the pitch and the yaw, only one combination is extracted for the pitch and the yaw as before, and a several patterns are extracted for the roll.

For the pitch and the yaw, as expressed in Expression 31 and Expression 32, only the postures closest to the average values of the pitch and the yaw of the triangle resulting from the triangulation are extracted. Here, the additional characters (f), (s), and (a) respectively represent the factory-produced data sets, the sample data sets, and the average of the three samples that constitute a triangle resulting from the triangulation, i represents the number of the factory-produced data set, j represents the number of the triangle resulting from the triangulation, and a number after j represents the number of an apex in the triangle.

For the roll, the extraction is performed only when an integer D' expressed in Expression 33 is a multiple of 3. That is, the extraction is performed at intervals of 7.5 [deg]. Here, a multiple of 3 is taken as the extraction condition because when taking multiples of an even number, the combinations of x, y, and z are limited based on the extraction condition described in <Dispersion Of Data Sets> as described above, and it is not possible to extract the rolls evenly, and because when taking multiples of a number equal to or greater than 5, the number of the extracted data sets for one position decreases too much.

Figure 26:
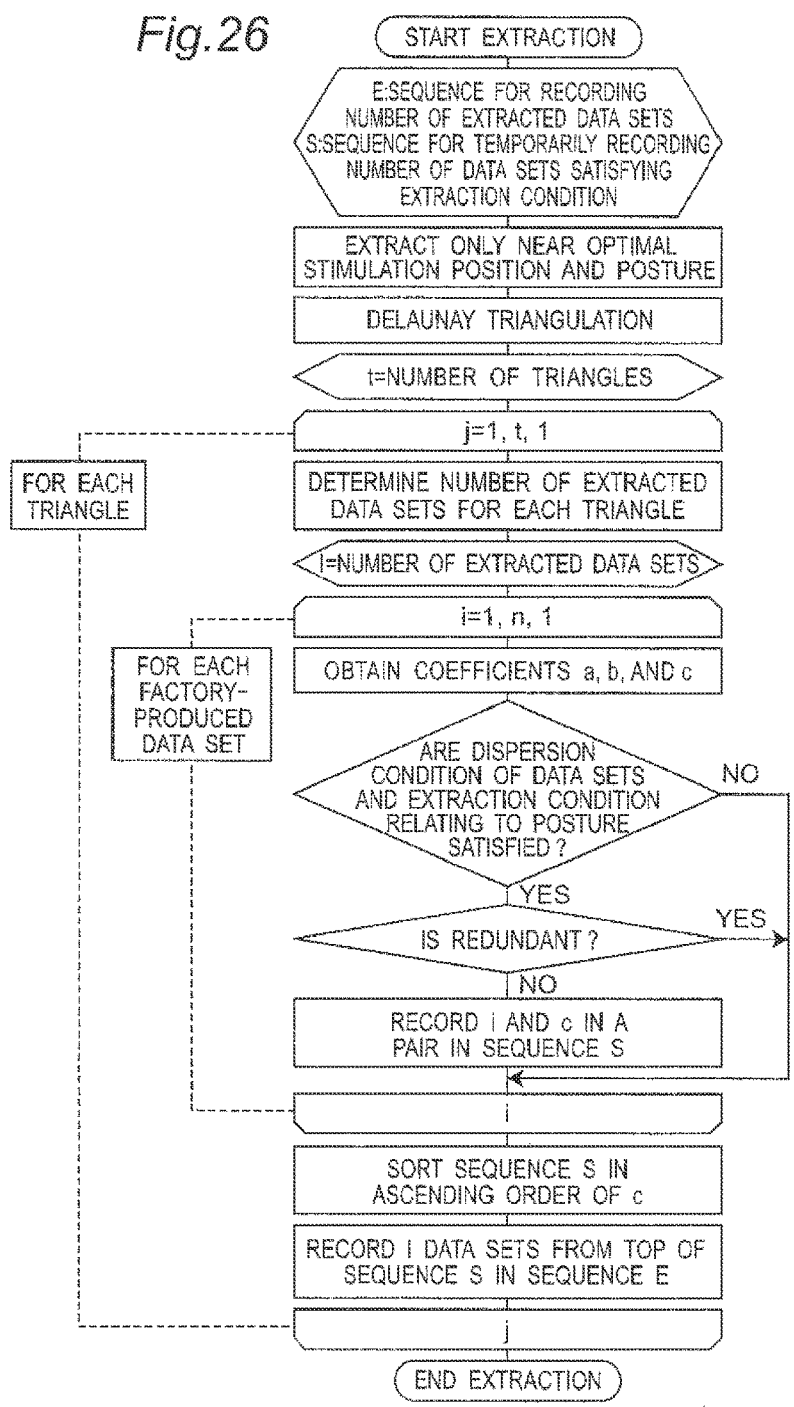
FIG. 26 is a flowchart for explaining a data set extraction procedure when the density adjustment is performed.

Based on the described above extraction condition, the extraction is performed. FIG. 26 shows a flow of the extraction program.

$$\begin{cases} \text{pitch}_j^{(a)} = (\text{pitch}_{j1}^{(s)} + \text{pitch}_{j2}^{(s)} + \text{pitch}_{j3}^{(s)})/3 \\ \text{yaw}_j^{(a)} = (\text{yaw}_{j1}^{(s)} + \text{yaw}_{j2}^{(s)} + \text{yaw}_{j3}^{(s)})/3 \end{cases}$$ [Expression 31]

$$\left|\text{pitch}_i^{(f)} - \text{pitch}_j^{(a)}\right| \le A, \left|\text{yaw}_i^{(f)} - \text{yaw}_j^{(a)}\right| \le A, A = \pi/144$$ [Expression 32]

$$D' = D + \frac{\text{roll}}{\pi/72} = \frac{x+y+z}{0.0025} + \frac{\text{roll}}{\pi/72}$$ [Expression 33]

<Extraction Result>

Figure 25:
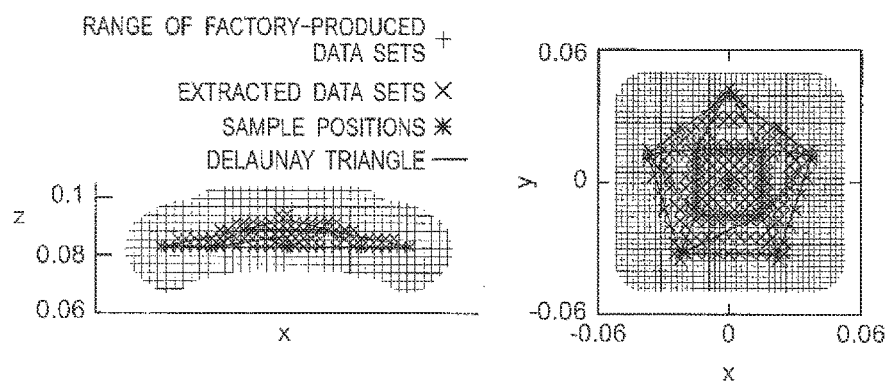
FIG. 25 shows explanatory diagrams illustrating data set extraction results when density adjustment is performed.

FIG. 25 shows a diagram plotting the positions of the extracted data sets using the chart generation tool GNU-PLOT. Further, the total numbers of the extracted data sets and the numbers of the extracted data sets for each triangle are shown in Table 8.

to FIG. 23(a) to FIG. 23(c), each show a charts grouping the extracted data sets by the radius $r=\sqrt{(x^2+y^2+z^2)}$ and the distance from the optimal stimulation position. A vertical axis in FIG. 27(a) and FIG. 27(b) represents the number of the extracted data sets, and a vertical axis in FIG. 27(c) represents an extraction density obtained by dividing the number of the extracted data sets by the cubic volume of the target range.

FIG. 28(a) to FIG. 28(c) each show a charts grouping the extracted data sets by the components of the roll, the pitch, and the yaw, and a vertical axis represents the number of the extracted data sets, while a horizontal axis represents a value of the posture by [deg]. However, the pitch and the yaw are relative values when the posture at which the magnetic coil faces the surface of the scalp is 0 (zero), instead of the values

TABLE 8

Number Of Extracted Data Sets For Each Triangle When Density Adjustment Is Performed

| Triangle No. | Apices Of Triangle | Distance From Optimal Stimulation Position To Barycenter [cm] | Area [mm²] | Number Of Extraction | Extraction Density [/mm²] | Total Ratio Of Extraction Density This Time | Total Ratio Of Extraction Density W = 1.25 |
|---|---|---|---|---|---|---|---|
| 1 | 1, 2, 3 | 1.014 | 228.1 | 837 | 3.6694 | | |
| | | Other Than Preferential extraction | | 322 | 1.4117 | 1.8701 | 1.1209 |
| 2 | 1, 2, 4 | 1.014 | 228.1 | 836 | 3.6651 | | |
| | | Other Than Preferential extraction | | 322 | 1.4117 | 1.8701 | 1.1209 |
| 3 | 1, 3, 5 | 1.014 | 228.1 | 836 | 3.6651 | | |
| | | Other Than Preferential extraction | | 322 | 1.4117 | 1.8701 | 1.1209 |
| 4 | 1, 4, 5 | 1.014 | 228.1 | 837 | 3.6694 | | |
| | | Other Than Preferential extraction | | 322 | 1.4117 | 1.8701 | 1.1209 |
| 5 | 2, 3, 9 | 2.253 | 273.0 | 173 | 0.6337 | 0.8395 | 1.0980 |
| 6 | 3, 9, 10 | 2.775 | 409.5 | 211 | 0.5153 | 0.6826 | 0.9904 |
| 7 | 2, 4, 7 | 2.326 | 345.7 | 212 | 0.6132 | 0.8124 | 1.1222 |
| 8 | 2, 7, 9 | 2.820 | 322.6 | 163 | 0.5053 | 0.6693 | 0.8472 |
| 9 | 3, 5, 8 | 2.326 | 345.7 | 212 | 0.6132 | 0.8124 | 1.1222 |
| 10 | 3, 8, 10 | 2.820 | 322.6 | 163 | 0.5053 | 0.6693 | 0.8472 |
| 11 | 4, 5, 6 | 2.370 | 382.4 | 231 | 0.6041 | 0.8002 | 1.1297 |
| 12 | 4, 6, 7 | 2.910 | 287.1 | 141 | 0.4911 | 0.6506 | 0.7063 |
| 13 | 5, 6, 8 | 2.910 | 287.1 | 141 | 0.4911 | 0.6506 | 0.7063 |
| Total | | | 3888.1 | 4993 | 1.2842 | | |
| | | Other Than Preferential extraction | | 2935 | 0.7549 | 1.0000 | 1.0000 |

*The preferential extraction refers to extraction performed first near the optimal stimulation position and posture Considering the disproportionality of the data sets to a specific triangle, side, or apex, it can be seen from FIG. 25 that the disproportionality of the extraction to a specific side or apex is overall reduced while there is still a hole in the extraction slightly. Further, it can be seen from Table 8 that an extra number of data sets are extracted in the triangles near the optimal stimulation position. Moreover, the numbers of extraction for the triangles 12 and 13 were extremely small in Table 7 shown above, there are no triangle for which the number of the extracted data sets is extremely smaller than other triangles this time (in Table 8).

Further, FIG. 27 and FIG. 28 show distribution charts of the extracted data set. FIG. 27(a) to FIG. 27(c) are, similarly in the actual data sets, and values in Expression 34 and Expression 35 expressed by Pitch and Yaw that are values in the actual data sets. Further, in the bar charts in FIG. 27 and FIG. 28, hatching by sold lines indicates the data sets that are extracted preferentially at the optimal stimulation position and posture, and hatching by dashed lines indicates the data sets that are extracted after the approximation of the surface of the scalp by Delaunay triangulation.

$$\text{pitch} = \text{Pitch} - \sin^{-1}\frac{x}{\sqrt{x^2+y^2+z^2}} = \sin^{-1}\frac{x}{r}$$ [Expression 34]

$$\text{yaw} = \text{Yaw} - \sin^{-1}\frac{y}{\sqrt{y^2+z^2}} \qquad \text{[Expression 35]}$$

Similarly to the extraction result shown in FIG. 23, it can be seen from FIG. 27(a) that the data sets along the surface of the scalp of the imaginary patient, which is a spherical form having the radius r=9 [cm], are extracted. Further, it can be seen from FIG. 27(c) that by performing the preferential extraction near the optimal stimulation position and posture, more data sets are extracted near the optimal stimulation position than the case of FIG. 23(c). Moreover, it can be seen from FIG. 28(a) that other than the data sets extracted by the preferential extraction, data sets having various roll values are evenly extracted. It can also be seen from FIG. 28(b) and FIG. 28(c) that data sets with the posture facing the surface of the scalp are mainly extracted.

From the above results, it was confirmed that based on these extraction conditions, it is possible to perform the extraction according to the conditions satisfied by the data set group considered to be required for the navigation described in <Data Set Extraction Condition> described above.

It should be noted that in the above embodiment, the factory-produced data sets are generated by the computer having the CPU (Central Processing Unit) shown in Table 2 built therein and the used software also shown in Table 2 installed therein. Instead, similarly to the conventional data set collection method, it is possible to collect the factory-produced data sets by simultaneous measurement using a three-dimensional measurement system such as an optical tracking system and a magnetic sensor.

In the above description, so-called Delaunay triangulation is used in order to estimate the shape of the surface of the scalp from a limited number of sample magnetic field data (that is, simulation samples thereof) collected by the doctor in the hospital from the surface of the patient's scalp when extracting a data set within an appropriate range required for obtaining the three-dimensional position and posture of the magnetic coil corresponding to the optimal stimulation position and posture for an individual patient ("custom data set" for each patient) from a large number of factory-produced data sets that have been collected, as well as in order to estimate the shape of the surface of the scalp from the samples when extracting the data set along the surface.

The method of estimating the shape of the surface of the scalp from the samples is not limited to the method of approximating to the surface of the scalp using Delaunay triangulation, and other methods utilizing other shapes are also applicable.

For example, shapes that are more resembled to the head shape than a group of triangles include an ellipsoid, and a method based on ellipsoidal approximation may be conceived as a method utilizing this shape. Next, a method of estimating the shape of the surface of the scalp using the "method based on the ellipsoidal approximation of the patient's head", and extracting the data sets along the surface will be described.

It should be noted that in the data set extraction method described hereinafter, when collecting the factory-produced data sets, the conventional data set collection method of collecting the factory-produced data sets by simultaneous measurement using a three-dimensional measurement system such as an optical tracking system and a magnetic sensor is employed.

[Ellipsoidal Approximation of Patient's Head]

Parameters required for determining one ellipsoid are six including center coordinates ($x_0$, $y_0$, $z_0$) of the ellipsoid, and radii a, b, and c in the three axis directions, and an ellipsoid may be expressed by Expression 36 using these parameters.

$$\frac{(x-x_0)^2}{a^2} + \frac{(y-y_0)^2}{b^2} + \frac{(z-z_0)^2}{c^2} = 1 \qquad \text{[Expression 36]}$$

Six parameters of an ellipsoid with a smallest error with respect to the samples collected by the doctor in the hospital are obtained by applying a method of least squares. When an approximate ellipsoid is expressed by Expression 36, a three-dimensional position of each sample is ($x_i$, $y_i$, $z_i$), the number of samples is n, a parameter as an error between a position of each sample and the approximate ellipsoid is $\varepsilon_i$, and the parameter $\varepsilon_i$ is defined as expressed by Expression 37. At this time, six parameters ($x_0$, $y_0$, $z_0$, a, b, c) for an ellipsoid whose value of $\Psi$ expressed by Expression 38 is smallest are obtained.

$$\varepsilon_i = \frac{(x_i-x_0)^2}{a^2} + \frac{(y_i-y_0)^2}{b^2} + \frac{(z_i-z_0)^2}{c^2} - 1 \qquad \text{[Expression 37]}$$

$$\Psi = \sum (\varepsilon_i)^2 \qquad \text{[Expression 38]}$$

When performing variable transformation as listed below in order to linearize the parameters, Expression 37 is altered to Expression 39.

$A_0 = 1/a^2$ $A_1 = -2x_0/a^2$ $B_0 = 1/b^2$ $B_1 = -2y_0/b^2$ $C_0 = 1/c^2$ $C_1 = -2z_0/c^2$ $D = (x_0^2/a^2) + (y_0^2/b^2) + (z_0^2/c^2)$

Then, the linearized parameters ($A_0$, $A_1$, $B_0$, $B_1$, $C_0$, $C_1$, D) are obtained so as to establish Expression 40.

$$\varepsilon_i = x_i^2 A_0 + x_i A_1 + y_i^2 B_0 + y_i B_1 + z_i^2 C_0 + z_i C_1 + D - 1 \qquad \text{[Expression 39]}$$

$$\partial\Psi/\partial A_0 = \partial\Psi/\partial A_1 = \ldots = \partial\Psi/\partial D = 0 \qquad \text{[Expression 40]}$$

Expression 41 may be obtained in simultaneous equations. However, a solution derived as it is becomes as follows.

$$A_0 = A_1 = B_0 = B_1 = C_0 = C_1 = 0, D = 1$$

Therefore, terms are transpositioned to obtain simultaneous equations in Expression 42.

$$\begin{bmatrix} \sum x_i^4 & \sum x_i^3 & \sum x_i^2 y_i^2 & \sum x_i^2 y_i & \sum x_i^2 z_i^2 & \sum x_i^2 z_i & \sum x_i^2 \\ \sum x_i^3 & \sum x_i^2 & \sum x_i y_i^2 & \sum x_i y_i & \sum x_i z_i^2 & \sum x_i z_i & \sum x_i \\ \sum x_i^2 y_i^2 & \sum x_i y_i^2 & \sum y_i^4 & \sum y_i^3 & \sum y_i^2 z_i^2 & \sum y_i^2 z_i & \sum y_i^2 \\ \sum x_i^2 y_i & \sum x_i y_i & \sum y_i^3 & \sum y_i^2 & \sum y_i z_i^2 & \sum y_i z_i & \sum y_i \\ \sum x_i^2 z_i^2 & \sum x_i z_i^2 & \sum y_i^2 z_i^2 & \sum y_i z_i^2 & \sum z_i^4 & \sum z_i^3 & \sum z_i^2 \\ \sum x_i^2 z_i & \sum x_i z_i & \sum y_i^2 z_i & \sum y_i z_i & \sum z_i^3 & \sum z_i^2 & \sum z_i \\ \sum x_i^2 & \sum x_i & \sum y_i^2 & \sum y_i & \sum z_i^2 & \sum z_i & n \end{bmatrix} \begin{bmatrix} A_0 \\ A_1 \\ B_0 \\ B_1 \\ C_0 \\ C_1 \\ D \end{bmatrix} = \begin{bmatrix} \sum x_i^2 \\ \sum x_i \\ \sum y_i^2 \\ \sum y_i \\ \sum z_i^2 \\ \sum z_i \\ n \end{bmatrix}$$ [Expression 41]

$$\begin{bmatrix} \sum x_i^4 & \sum x_i^3 & \sum x_i^2 y_i^2 & \sum x_i^2 y_i & \sum x_i^2 z_i^2 & \sum x_i^2 z_i \\ \sum x_i^3 & \sum x_i^2 & \sum x_i y_i^2 & \sum x_i y_i & \sum x_i z_i^2 & \sum x_i z_i \\ \sum x_i^2 y_i^2 & \sum x_i y_i^2 & \sum y_i^4 & \sum y_i^3 & \sum y_i^2 z_i^2 & \sum y_i^2 z_i \\ \sum x_i^2 y_i & \sum x_i y_i & \sum y_i^3 & \sum y_i^2 & \sum y_i z_i^2 & \sum y_i z_i \\ \sum x_i^2 z_i^2 & \sum x_i z_i^2 & \sum y_i^2 z_i^2 & \sum y_i z_i^2 & \sum z_i^4 & \sum z_i^3 \\ \sum x_i^2 z_i & \sum x_i z_i & \sum y_i^2 z_i & \sum y_i z_i & \sum z_i^3 & \sum z_i^2 \end{bmatrix} \begin{bmatrix} A_0/(1-D) \\ A_1/(1-D) \\ B_0/(1-D) \\ B_1/(1-D) \\ C_0/(1-D) \\ C_1/(1-D) \end{bmatrix} = \begin{bmatrix} \sum x_i^2 \\ \sum x_i \\ \sum y_i^2 \\ \sum y_i \\ \sum z_i^2 \\ \sum z_i \end{bmatrix}$$ [Expression 42]

The simultaneous equations expressed by Expression 42 is solved by Gaussian elimination, and the obtained linearized parameters ($A_0$, $A_1$, $B_0$, $B_1$, $C_0$, $C_1$, $D$) are again converted into the original ellipsoid parameters ($x_0$, $y_0$, $z_0$, $a$, $b$, $c$). First, the center coordinates ($x_0$, $y_0$, $z_0$) of the approximate ellipsoid are respectively expressed by Expression 43, Expression 44, and Expression 45 based on the above expression for variable transformation for the linearized parameters ($A_0$, $A_1$, $B_0$, $B_1$, $C_0$, $C_1$, $D$). Then, the radii $a$, $b$, and $c$ in the three axis directions are respectively expressed by Expression 46, Expression 47, and Expression 48.

$$x_0 = \frac{A_1/(1-D)}{2A_0/(1-D)}$$ [Expression 43]

$$y_0 = \frac{B_1/(1-D)}{2B_0/(1-D)}$$ [Expression 44]

$$z_0 = \frac{C_1/(1-D)}{2C_0/(1-D)}$$ [Expression 45]

$$a = \frac{1}{\sqrt{\frac{1}{A_0/(1-D)} + x_0^2 + \frac{B_0/(1-D)}{A_0/(1-D)} y_0^2 + \frac{C_0/(1-D)}{A_0/(1-D)} z_0^2}}$$ [Expression 46]

$$b = \frac{1}{\sqrt{\frac{1}{B_0/(1-D)} + \frac{A_0/(1-D)}{B_0/(1-D)} x_0^2 + y_0^2 + \frac{C_0/(1-D)}{B_0/(1-D)} z_0^2}}$$ [Expression 47]

$$c = \frac{1}{\sqrt{\frac{1}{C_0/(1-D)} + \frac{A_0/(1-D)}{C_0/(1-D)} x_0^2 + \frac{B_0/(1-D)}{C_0/(1-D)} y_0^2 + z_0^2}}$$ [Expression 48]

Taking an approximate ellipsoid model of the head shape thus obtained as a standard, the three-dimensional position components (x, y, z) of each of the factory-produced data sets are converted into polar coordinates (r, θ, φ), and determined whether or not this target factory-produced data set is required for the navigation. The polar coordinates transformation may be performed using relations expressed by Expression 49, Expression 50, and Expression 51.

$$r^2 = \frac{(x-x_0)^2}{a^2} + \frac{(y-y_0)^2}{b^2} + \frac{(z-z_0)^2}{c^2}$$ [Expression 49]

$$\theta = \sin^{-1}\{(x-x_0)/ra\}$$ [Expression 50]

$$\varphi = \sin^{-1}\{(y-y_0)/rb\}$$ [Expression 51]

If r=1 in Expression 49, this matches Expression 36, and this indicates that the target factory-produced data set is immediately above the approximate ellipsoid. Alternatively, it is indicated that the target factory-produced data set is within the head if r<1, and that the target factory-produced data set is outside the head if r>1.

The parameters (θ, φ) shown in Expression 50 and Expression 51 represent Cartesian coordinates on the surface of the scalp, and it is indicated that the closer to the values of (θ, φ) for a data set at the optimal stimulation position, the closer the target factory-produced data set is to the optimal stimulation position.

Figure 29:
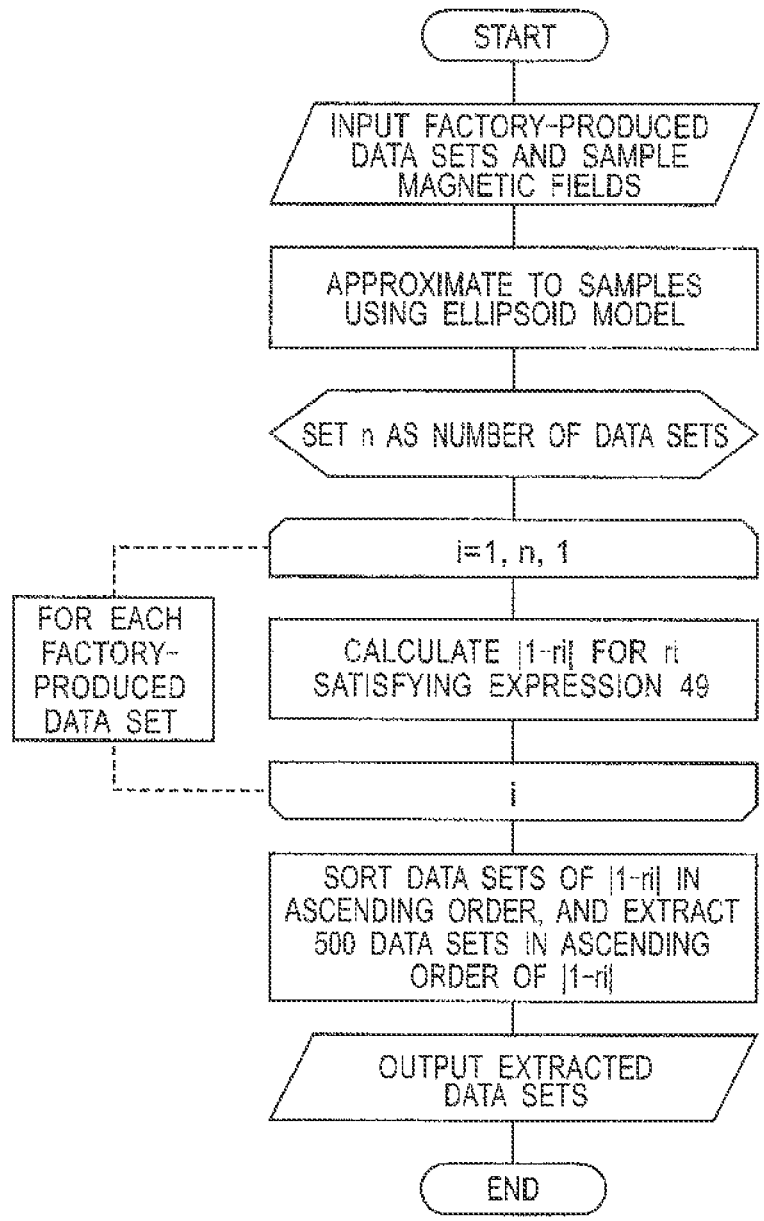
FIG. 29 is a flowchart for explaining a data set extraction procedure near the approximate surface of the scalp based on ellipsoidal approximation.

FIG. 29 shows a flow of selection of the extracted data sets. In FIG. 29, i represents the number of the factory-produced data sets, and $r_i$ represents a value satisfying Expression 49. Absolute values of $(1-r_i)$ are obtained for the respective factory-produced data sets, and the absolute values are sorted, for example, in ascending order, and 500 data sets are extracted in ascending order.

[Accuracy Evaluation of Magnetic Field Navigation System]

In order to ensure a treatment effect by the transcranial magnetic stimulation treatment, it is required that deviation of a central position of the magnetic field of the treatment coil with respect to a target site corresponding to the optimal stimulation position be within 5 [mm], and deviation of the posture of the treatment coil with respect to the optimal coil posture (roll angle, pitch angle, and yaw angle) be within 5 [deg].

Total accuracy evaluation as a system was performed in view of the positioning accuracy on completion of the navigation toward the practical use of a magnetic field type navigation system. Specifically, the optimal stimulation position of the coil is termed as a "target", the actual position of the coil on completion of the navigation is termed as an "actual measurement value", and the position of the coil on completion of the navigation estimated by the system using the data sets is termed as an "estimation value", and the following four points were tested.

(a) Deviation between the actual measurement value and the target (navigation accuracy of the system)

(b) Deviation between the actual measurement value and the estimation value (measurement accuracy of the system on completion of the navigation)

(c) An influence given to the navigation accuracy by the number of data sets (d) An influence given to the sensor by an application of the magnetic field by the stimulation coil It should be noted that, the actual positions of the target and the coil (actual measurement value) are measured by an optical three-dimensional measurement device Polaris (that is, Polaris is used as a system for accuracy evaluation of the magnetic field type navigation system). Further, the navigation was performed based on the setting of "a distance error within 1 [mm] and an angle error within 5 [deg]".

[Stimulation Positioning System]

<Coil Positioning System (Method Based on Ellipsoidal Approximation of the Patient's Head)>

An experimentation of performing a visual test by plotting the positions of the extracted data sets and a practical test by the navigation on the head model using the extracted data sets for both of the "data set extraction method using ellipsoidal approximation" and the "data set extraction method using Delaunay triangulation", and performances of these were compared.

In the visual test, first, 15,000 factory-produced data sets and 30 samples obtained from the surface of the head model were prepared using four magnetic sensors (AMI302 manufactured by Aichi Steel Corporation). 10 samples used for the data set extraction were selected randomly from the above, and an experimentation of extracting 500 data sets from the same factory-produced data sets using the same samples in the both methods was performed. Influences on the extracted data sets by randomly changing arrangement of the samples were compared for each of methods.

FIG. 30 shows diagrams plotting three-dimensionally one example of the data set extraction result using arbitrary 10 samples. FIG. 30(a) shows a case of ellipsoidal approximation, and FIG. 30(b) shows a case of using Delaunay triangulation, where top views are shown on the left and side views are shown on the right. The factory-produced data sets and the samples used are the same in either case.

In comparison between the data set extraction results in this example, no significant difference is found in the plotted diagrams, but slight disproportionality of the extraction is found in the result of Delaunay triangulation. Further, there is a tendency that ellipsoidal approximation allows extraction of more data sets better fit for the shape of the head.

Figure 31:
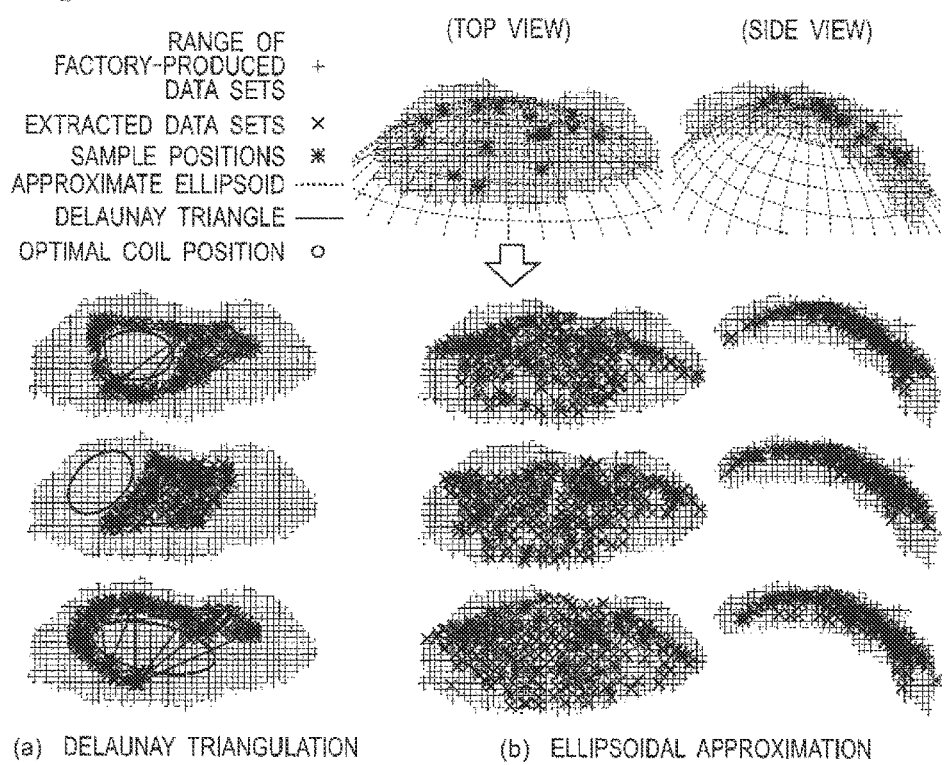
FIG. 31 shows explanatory diagrams illustrating data set extraction results when an arrangement of the samples is varied, in which (a) shows an extraction result using Delaunay triangulation, and (b) shows an extraction result using the ellipsoidal approximation.

FIG. 31 shows data set extraction results (total 3 patterns) in a case in which positions of the samples are randomly changed. While an influence of the positions of the samples is relatively large in the case of Delaunay triangulation, there is only a small influence by the positions of the samples in the case of ellipsoidal approximation as illustrated in FIG. 31 (b). From this result, it can be said that the method based on ellipsoidal approximation is able to have a larger degree of freedom in the positions of the samples than the method using Delaunay triangulation, and it is possible to significantly reduce the burden for the doctor involved in the initial treatment (a stable extraction result may be always obtained even if the doctor collects the samples in a reasonable manner).

Further, in the practical test, the navigation was more smoothly performed in the ellipsoidal approximation. In the case of Delaunay triangulation, as suitable data sets were not extracted at a position distant from the positions of the samples, there was a case in which the position of the stimulation coil was not able to grasp. It should be noted that in either case, the data sets near the optimal stimulation position are extracted preferentially, final navigation accuracy does not change.

<Accuracy Evaluation of Magnetic Field Type Navigation System>

[Experimentation 1]

Evaluation of Measurement Accuracy and Navigation Accuracy on Completion of the Navigation Using four normal magnetic sensors (AMI302 manufactured by Aichi Steel Corporation), the navigation experiment was performed total 13 times according to the following process under a common termination condition that "a distance error within 1 [mm], an angle error (for each of the angles of roll, pitch, and yaw) within 5 [deg]" with respect to the same optimal stimulation position.

(a) After manually collecting 500 data sets (pattern 1), the navigation was performed 5 times using the data sets of the pattern 1

(b) After manually collecting 500 data sets (pattern 2), the navigation was performed 5 times using the data sets of the pattern 2

(c) After manually collecting 500 data sets (pattern 3), the navigation was performed 3 times using the data sets of the pattern 3

For each navigation described above, using the optical measurement device Polaris, the optimal stimulation position (target: common to all trials) and the three-dimensional position and the posture of the coil after the navigation has completed (actual measurement value) were measured. Further, the three-dimensional position and the posture of the coil on completion of the navigation when the system has estimated using the data sets (estimation value) was also recorded for each trial.

FIG. 32 shows results of the experimentation. FIG. 32(a) shows deviation between the actual measurement values and the estimation values, and FIG. 32(b) shows deviation between the actual measurement values and the targets. It should be noted that each of values in parentheses in FIG. 32(b) indicate a distance from the target estimated by the system (unit [mm]). As the termination condition of the navigation is "the error within 1 [mm]", it should be noted that these values are always equal to or smaller than 1 [mm].

In all of the 13 trials, the deviation between the actual measurement values and the estimation values (that is, the measurement accuracy on completion of the navigation) was within 4 [mm], and the deviation between the actual measurement values and the targets (that is, the navigation accuracy for the distance error) was also within 5 [mm]. Further, although not shown in FIG. 32(a) and FIG. 32(b), the navigation accuracy for the angle errors was within 5 [deg] in the all trial for the roll angle, the pitch angle, and the yaw angle.

As described above, it was confirmed that according to this embodiment, the navigation accuracy required in order to ensure the treatment effect by the transcranial magnetic stimulation treatment was achieved with regard to any of the distance error and the angle errors.

There was a learning effect as the data sets were collected manually, and there was a tendency that both the distance error and the error dispersion were reduced more in the pattern 2 than in the pattern 1, and more in the pattern 2 than in the pattern 3.

It is envisaged that the extraction of 500 data sets is actually performed automatically by the system based on such a method using ellipsoidal approximation, and therefore a level of the navigation accuracy of the pattern 3 (the distance error within 2 [mm]) is expected.

[Experimentation 2]

Tests of an influence of the number of data sets given to the navigation accuracy and an influence of application of the magnetic field by the stimulation coil given to the magnetic sensors Using total four magnetic sensors (AMI302 manufactured by Aichi Steel Corporation) including one magnetic sensor to which a magnetic field is previously applied by a stimulation coil by placing the stimulation coils on the magnetic sensor, the navigation experiment was performed two times according to the following process under the common termination condition that "the distance error within 1 [mm] and the angle error (for each of the roll angle, the pitch angle, and the yaw angle) within 5 [deg]" with respect to the same optimal stimulation position.

(a) After manually collecting 200 data sets, the navigation was performed once using these data sets (b) After manually collecting 500 data sets, the navigation was performed once using these data sets Using the optical measurement device Polaris, the optimal stimulation position (target: common to all trials) and the three-dimensional position and the posture of the coil after the navigation has completed (actual measurement value) were measured. Further, the three-dimensional position and the posture of the coil on completion of the navigation when the system has estimated using the data sets (estimation value) was also recorded for each trial.

[Experimentation Result]

When 200 data sets were manually collected, the distance error (the deviation between the actual measurement values and the targets) was within 5.30 [mm], and when 500 data sets were manually collected, the distance error was within 2.11 [mm]. For the angle errors, the error was within 5 [deg] for any of the roll angle, the pitch angle, and the yaw angle under either condition.

From the above results, it is considered that the magnetic sensor to which the magnetic field is applied by the stimulation coil also operates normally like other magnetic sensors. However, in the case of this experimentation, it is difficult to achieve "the distance error within 5 [mm]" with the 200 data sets, and it is suggested that this number is insufficient as the number of data sets in the navigation. It is desirable that the number of data sets should be 500 or more.

According to this embodiment, in the data set type magnetic field navigation system, in order to significantly reduce the time and effort involved in the process of data set collection for each patient that may possibly become a burden for the doctor, a large amount of data set group called as the factory-produced data sets considered to be applied to any patient is prepared, and data sets required for the navigation with the patient are extracted using information of samples of a magnetic field obtained from a surface of a scalp of a specific patient.

From various extraction results, it is confirmed that the data set extraction on the surface of the approximation scalp using Delaunay triangulation is especially effective, and that it is possible to extract the data set group considered to be required for navigation in combination with several other conditions.

Further, by performing the approximation of the shape of the surface of the scalp of the patient based on ellipsoidal approximation, it is possible to perform the data set extraction as effective as or more effective than the data set extraction on the surface of the approximation scalp using Delaunay triangulation.

Moreover, in the above embodiment, basically, the magnetic coil is operated and relatively displaced with respect to the fixed patient's head. However, instead of this, it is possible to configure such that the magnetic coil is fixed, and the patient's head is relatively displaced with respect to the fixed magnetic coil. Alternatively, the present invention may be effectively applied to a case in which both of the patient's head and the magnetic coil are operated and relatively displaced with respect to each other.

As one example of such an embodiment, the positioning procedure to the optimal stimulation position, in particular, in the home treatment is exemplified as follows.

First, similarly to the above embodiment, magnetic field sensors as the magnetic field detecting means are fixed to the patient's head using the fixing means such as a pair of eyeglasses. On the other hand, magnetic coils are fixed by the holder fixation member so as to roughly face against stimulation position over the head (for example, a region corresponding to primary motor cortex). After the completion of the above setting, the patient moves own head so as to correspond to the optimal stimulation position. Then, similarly to the above embodiment, the deviation from the optimal stimulation position and posture of the magnetic coil (misalignment) is detected.

In this case, the user interface section instructs the patient how the patient should move own head. Specifically, the movement of the patient's head is navigated so that the magnetic coil takes the optimum position and posture. Through this process, similarly to the above embodiment, it is possible to perform the treatment at the optimal stimulation position.

It should be noted that the magnetic coil may be operated to be displaced along with the patient moving the own head. In this case, by the user interface section functioning both as the instructing means for guiding the displacement operation of the magnetic coil and the instructing means for guiding the movement of the patient's head, it is possible to effectively perform the navigation of the magnetic coil to the optimal stimulation position and posture.

Further, the above embodiments are described with regard to the cases used in the transcranial magnetic stimulation treatment for relieving neuropathic pain by applying the magnetic stimulation to brain nerve by the magnetic coils placed over the surface of the scalp of the patient. However, the present invention is not limited to such a case, and may be effectively applied to a different application of magnetic stimulation.

As described above, the present invention is not limited to the above embodiments, and it should be appreciated that various modifications or improvements in design may be made to the present invention without departing from the spirit of the invention.

INDUSTRIAL APPLICABILITY

The present invention relates to a therapeutic electromagnetic stimulation device for providing magnetic stimulation by applying a magnetic field to a specific site of an object person, and effectively utilized, for example, as a device used in transcranial magnetic stimulation treatment for applying magnetic stimulation to brain nerve by magnetic coils placed over a surface of a scalp of a patient, or as a method of generating custom data pairs used in this device for each object person.

DESCRIPTION OF REFERENCE SYMBOLS

10 TRANSCRANIAL MAGNETIC STIMULATION APPARATUS
11 MAGNETIC COIL
12 COIL HOLDER
13 MAGNETIC FIELD SENSOR
14 PAIR OF EYEGLASSES
16 MAGNETIC STIMULATION CONTROL DEVICE
20 DATA SET ANALYZING UNIT
22 SIGNAL ANALYZING SECTION
23 RECORDING SECTION
24 COMPARING SECTION
25 USER INFORMATION OUTPUT SECTION
28 USER INTERFACE SECTION
M PATIENT

The invention claimed is:

1. A therapeutic transcranial electromagnetic stimulation device for providing magnetic stimulation by applying a magnetic field to a specific site of a head of a person, the device comprising:

therapeutic magnetic field generating means;

magnetic field detecting means respectively disposed so as to take a specific relative position with respect to the person in order to detect intensities of components in a plurality of directions of the magnetic field at least at two detection positions, the magnetic field being generated by the therapeutic magnetic field generating means;

a recording means configured to previously record parent data pairs which are defined as data pairs of information (a) and information (b), the information (a) being composed of at least information of a three-dimensional position of the therapeutic magnetic field generating means, the information (b) being composed of information of recorded component intensities, the recorded component intensities being defined as intensities of components of the magnetic field detected by the magnetic field detecting means, and the magnetic field being generated by the therapeutic magnetic field generating means disposed at the three-dimensional position;

a comparing means configured to perform an approximation of a shape of a surface of a scalp of the person based on first sampling component intensities, and further to extract custom data pairs for the person from the previously recorded parent data pairs, by using the first sampling component intensities in such a state that the therapeutic magnetic field generating means are disposed at sampling positions near the specific site of the head of the person, the custom data pairs being defined as data pairs which are close to the approximated shape of the surface of the scalp, and the first sampling component intensities resulting from sampling intensities detected by the magnetic field detecting means, wherein the comparing means is further configured to compare second sampling component intensities with the extracted custom data pairs, to detect deviation of the positions of the therapeutic magnetic field generating means from optimum stimulation positions, and further to generate instruction information to perform a displacement operation using the therapeutic magnetic field generating means, the second sampling component intensities being defined as intensities of the magnetic field detected by the magnetic field detecting means prior to the magnetic stimulation or during the magnetic stimulation.

2. The therapeutic transcranial electromagnetic stimulation device according to claim 1, wherein
a number of the extracted custom data pairs is within a range from 500 to 5000.

3. The therapeutic transcranial electromagnetic stimulation device according to claim 1, wherein
the approximation of the shape of the surface of the scalp of the person is performed based on Delaunay triangulation, the approximation being performed on such an occasion that the comparing means extracts the custom data pairs.

4. The therapeutic transcranial electromagnetic stimulation device according to claim 3, wherein
the comparing means is further configured to generate the custom data pairs by extracting data sets, of the parent data pairs, in ascending order of a respective distance between a triangle, produced by the Delaunay triangulation, and each triangle produced by a Delaunay triangulation of the extracted data sets, and
wherein the distance is a normal unit vector.

5. The therapeutic transcranial electromagnetic stimulation device according to claim 4, wherein
the comparing means is further configured to arrange the extracted data sets at intervals of 2.5 mm in a grid pattern.

6. The therapeutic transcranial electromagnetic stimulation device according to claim 4, wherein
the comparing means is further configured to extract at least 500 of the parent data pairs and at most 5000 of the parent data pairs.

7. The therapeutic electromagnetic stimulation device according to claim 1, wherein
the approximation of the shape of the surface of the scalp of the person is performed based on ellipsoidal approximation, the approximation being performed on such an occasion that the comparing means extracts the custom data pairs.

8. The therapeutic transcranial electromagnetic stimulation device according to claim 1 wherein
the recorded component intensities, the first sampling component intensities and the second sampling component intensities are for detection of positional information and angle information,
the magnetic field detecting means are disposed to take specific relative positions and specific relative angles with respect to the person,
the parent data pairs each include (a') information of a three-dimensional position and an inclination angle of the therapeutic magnetic field generating means pairing with (b') information of the recorded component intensities at the position and the inclination angle, and
the comparing means is further configured to generate the custom data pairs for each person from the previously recorded parent data pairs, the custom data pairs being for deriving the information of the position and the inclination angle of the therapeutic magnetic field generating means.

9. The therapeutic transcranial electromagnetic stimulation device according to claim 1 wherein the recorded component intensities, the first sampling component intensities and the second sampling component intensities are for detection of positional information, the magnetic field detecting means are disposed to take specific relative positions and specific relative angles with respect to the person, the parent data pairs each include (a') information of a three-dimensional position of the therapeutic magnetic field generating means pairing with (b') information of the recorded component intensities at the position, the comparing means is further configured to generate the custom data pairs for each person from the previously recorded parent data pairs, the custom data pairs being for deriving the information of the position of the therapeutic magnetic field generating means, and detection of an inclination angle of the therapeutic magnetic field generating means is performed by a measuring means configured to measure the inclination angle of the therapeutic magnetic field generating means separately from the generation and the detection of the magnetic field.

10. A therapeutic transcranial electromagnetic stimulation device for providing magnetic stimulation by applying a magnetic field to a specific site of a head of a person, the device comprising:

therapeutic magnetic field generating means;

magnetic field detecting means respectively disposed so as to take a specific relative position with respect to the person in order to detect intensities of components in a plurality of directions of the magnetic field at least at two detection positions, the magnetic field being generated by the therapeutic magnetic field generating means;

a recording means configured to previously record parent data pairs which are defined as data pairs of information (a) and information (b), the information (a) being composed of at least information of a three-dimensional position of the therapeutic magnetic field generating means, the information (b) being composed of information of recorded component intensities, the recorded component intensities being defined as intensities of components of the magnetic field detected by the magnetic field detecting means, and the magnetic field being generated by the therapeutic magnetic field generating means disposed at the three-dimensional position;

a comparing means configured to perform an approximation of a shape of a surface of a scalp of the person based on the previously recorded parent data pairs, and further to extract custom data pairs for the person from the previously recorded parent data pairs, by using first sampling component intensities in such a state that the therapeutic magnetic field generating means are disposed at sampling positions near the specific site of the head of the person, the custom data pairs being defined as data pairs which are close to the approximated shape of the surface of the scalp, and the first sampling component intensities resulting from sampling intensities detected by the magnetic field detecting means, wherein the comparing means is further configured to generate, using the extracted custom data pairs and second sampling component intensities, information for controlling a movement of the therapeutic magnetic field generating means to a position for an application of magnetic stimulation to the specific site of the head, the second sampling component intensities being defined as intensities of the magnetic field detected by the magnetic field detecting means prior to the magnetic stimulation or during the magnetic stimulation.

11. A method of generating custom data pairs used for a therapeutic transcranial electromagnetic stimulation device for providing magnetic stimulation by applying a magnetic field to a specific site of a head of a person, the device being provided with: therapeutic magnetic field generating means; and magnetic field detecting means respectively disposed so as to take a specific relative position with respect to the person in order to detect intensities of components in a plurality of directions of the magnetic field at least at two detection positions, the magnetic field being generated by the therapeutic magnetic field generating means or, the method comprising:

detecting the intensities of the corresponding components in a state in which the therapeutic magnetic field generating means are disposed respectively at a plurality of sampling spots near the specific site of the head of the person;

referring to a plurality of previously recorded parent data pairs based on a sampling detection result, the plurality of parent data pairs each including (a) at least information of a three-dimensional position of the therapeutic magnetic field generating means pairing with (b) information of the intensities of the corresponding components of the magnetic field at a position having at least the information of the three-dimensional position;

extracting custom data pairs for the person from the parent data pairs, by using first sampling component intensities in such a state that the therapeutic magnetic field generating means is disposed at sampling positions near the specific site of the head of the person;

approximating a shape of a surface of a scalp of the person based on the first sampling component intensities, the custom data pairs being defined as data pairs which are close to the shape of the surface of the scalp, and the first sampling component intensities resulting from sampling intensities detected by the magnetic field detecting means; and applying the therapeutic magnetic field adjusted according to an approximation of the shape.

12. The method of generating custom data pairs according to claim 11, wherein the specific site is a specific stimulation position within the head of the person, and a data generating means is configured to refer to the parent data pairs based on the sampling detection result.

13. The method of generating custom data pairs according to claim 12, wherein the approximation of the shape of the surface of the scalp of the person is performed based on Delaunay triangulation.

14. The method of generating custom data pairs according to claim 12, wherein the approximation of the shape of the surface of the scalp of the person is performed based on ellipsoidal approximation.

15. The method of generating custom data pairs according to claim 11, wherein the magnetic field is for detection of positional information and angle information, the magnetic field detecting means are disposed to take specific relative positions and specific relative angles with respect to the person, the parent data pairs each include (a') information of a three-dimensional position and an inclination angle of the magnetic field generating means pairing with (b') information of the intensities of the corresponding components of the magnetic field at the position and the inclination angle, and in generating the custom data pairs, the custom data pairs for deriving the information of the position and the inclination angle of the therapeutic magnetic field generating means are generated for the person.

16. The method of generating custom data pairs according to claim 11, wherein the magnetic field is for detection of positional information, the magnetic field detecting means are disposed to take specific relative positions and specific relative angles with respect to the person, the parent data pairs each include (a') information of a three-dimensional position and an inclination angle of the magnetic field generating means pairing with (b') information of the intensities of the corresponding components of the magnetic field at the position and the inclination angle, in generating the custom data pairs, the custom data pairs for deriving the information of the position and the inclination angle of the therapeutic magnetic field generating means are generated for the person, and the detection of the inclination angle of the therapeutic magnetic field generating means is performed by a measuring means configured to measure the inclination angle of the therapeutic magnetic field generating means separately from the generation and the detection of the magnetic field.

17. A therapeutic transcranial electromagnetic stimulation device for providing magnetic stimulation by applying a magnetic field to a specific site of a head of a person, the device comprising:

therapeutic magnetic field generating means;

detection magnetic field generating means;

a coil holder which holds the therapeutic magnetic field generating means and the detection magnetic field generating means;

magnetic field detecting means respectively disposed so as to take a specific relative position with respect to the person in order to detect intensities of components in a plurality of directions of the magnetic field at least at two detection positions, the magnetic field being generated by the detection magnetic field generating means configured to generate a detection magnetic field, and the detection magnetic field generating means being attached to the therapeutic magnetic field generating means;

a recording means configured to previously record parent data pairs which are defined as data pairs of information (a) and information (b), the information (a) being composed of at least information of a three-dimensional position of the therapeutic magnetic field generating means, the information (b) being composed of information of recorded component intensities, the recorded component intensities being defined as intensities of components of the magnetic field detected by the magnetic field detecting means, and the magnetic field being generated by the detection magnetic field generating means attached to the therapeutic magnetic field generating means disposed at the three-dimensional position;

a comparing means configured to perform an approximation of a shape of a surface of a scalp of the person based on first sampling component intensities, and further to extract custom data pairs for the person from the previously recorded parent data pairs, by using the first sampling component intensities in such a state that the therapeutic magnetic field generating means are disposed at sampling positions near the specific site of the head of the person, the custom data pairs being defined as data pairs which are close to the approximated shape of the surface of the scalp, and the first sampling component intensities resulting from sampling intensities detected by the magnetic field detecting means, wherein the comparing means is further configured to compare second sampling component intensities with the extracted custom data pairs, to detect deviation of the positions of the therapeutic magnetic field generating means from optimum stimulation positions, and further to generate instruction information to perform a displacement operation using the therapeutic magnetic field generating means, the second sampling component intensities being defined as intensities of the magnetic field detected by the magnetic field detecting means prior to the magnetic stimulation or during the magnetic stimulation.

* * * * *